United States Patent
Sazuka et al.

(10) Patent No.: US 8,321,146 B2
(45) Date of Patent: Nov. 27, 2012

(54) GENE CLASSIFYING METHOD, GENE CLASSIFYING PROGRAM, AND GENE CLASSIFYING DEVICE

(75) Inventors: Naoya Sazuka, Tokyo (JP); Takeshi Asakawa, Chiba (JP)

(73) Assignee: Sony Corporation, Tokyo (JP)

( * ) Notice: Subject to any disclaimer, the term of this patent is extended or adjusted under 35 U.S.C. 154(b) by 597 days.

(21) Appl. No.: 12/544,751

(22) Filed: Aug. 20, 2009

(65) Prior Publication Data
US 2010/0049446 A1 Feb. 25, 2010

(30) Foreign Application Priority Data

Aug. 21, 2008 (JP) .................................. 2008-213112
Dec. 19, 2008 (JP) .................................. 2008-324244

(51) Int. Cl.
*G06F 19/00* (2011.01)
*G06F 15/00* (2006.01)
*G11C 17/00* (2006.01)

(52) U.S. Cl. ................................. 702/19; 365/94; 700/1
(58) Field of Classification Search .................. None
See application file for complete search history.

(56) References Cited

FOREIGN PATENT DOCUMENTS

JP 2008-82876 4/2008

OTHER PUBLICATIONS

Sahoo et al. Extracting binary signals from microarray time-course data. Nucleic Acids Research vol. 35, pp. 3705-3712 (2007).*

* cited by examiner

*Primary Examiner* — John S Brusca
(74) *Attorney, Agent, or Firm* — K&L Gates LLP

(57) ABSTRACT

A gene classifying method is provided and includes acquiring expression levels of a plurality of genes at a plurality of observation points, generating a binary string by taking a positive or negative difference in expression level in a temporal passage direction of the observation points for each gene, and classifying the genes on the basis of all plus and minus patterns that the binary strings can have and the generated binary strings.

13 Claims, 18 Drawing Sheets

ENTIRE CONFIGURATION OF GENE ANALYSIS SYSTEM

HYBRIDIZATION IN NUCLEIC ACID TIP

CONFIGURATION OF GENE CLASSIFYING DEVICE

FIG.7

EXPRESSION CHANGE PATTERN WHEN THE NUMBER OF OBSERVATION POINTS IS 6

| | 1 | 2 | 3 | 4 | 5 | | 1 | 2 | 3 | 4 | 5 |
|---|---|---|---|---|---|---|---|---|---|---|---|
| 1 | + | + | + | + | + | 17 | − | − | − | − | − |
| 2 | − | + | + | + | + | 18 | + | − | − | − | − |
| 3 | + | − | + | + | + | 19 | − | + | − | − | − |
| 4 | + | + | − | + | + | 20 | − | − | + | − | − |
| 5 | + | + | + | − | + | 21 | − | − | − | + | − |
| 6 | + | + | + | + | − | 22 | − | − | − | − | + |
| 7 | − | − | + | + | + | 23 | + | + | − | − | − |
| 8 | − | + | − | + | + | 24 | + | − | + | − | − |
| 9 | − | + | + | − | + | 25 | + | − | − | + | − |
| 10 | − | + | + | + | − | 26 | + | − | − | − | + |
| 11 | + | − | − | + | + | 27 | − | + | + | − | − |
| 12 | + | − | + | − | + | 28 | − | + | − | + | − |
| 13 | + | − | + | + | − | 29 | − | + | − | − | + |
| 14 | + | + | − | − | + | 30 | − | − | + | + | − |
| 15 | + | + | − | + | − | 31 | − | − | + | − | + |
| 16 | + | + | + | − | − | 32 | − | − | − | + | + |

TEST RESULT 1

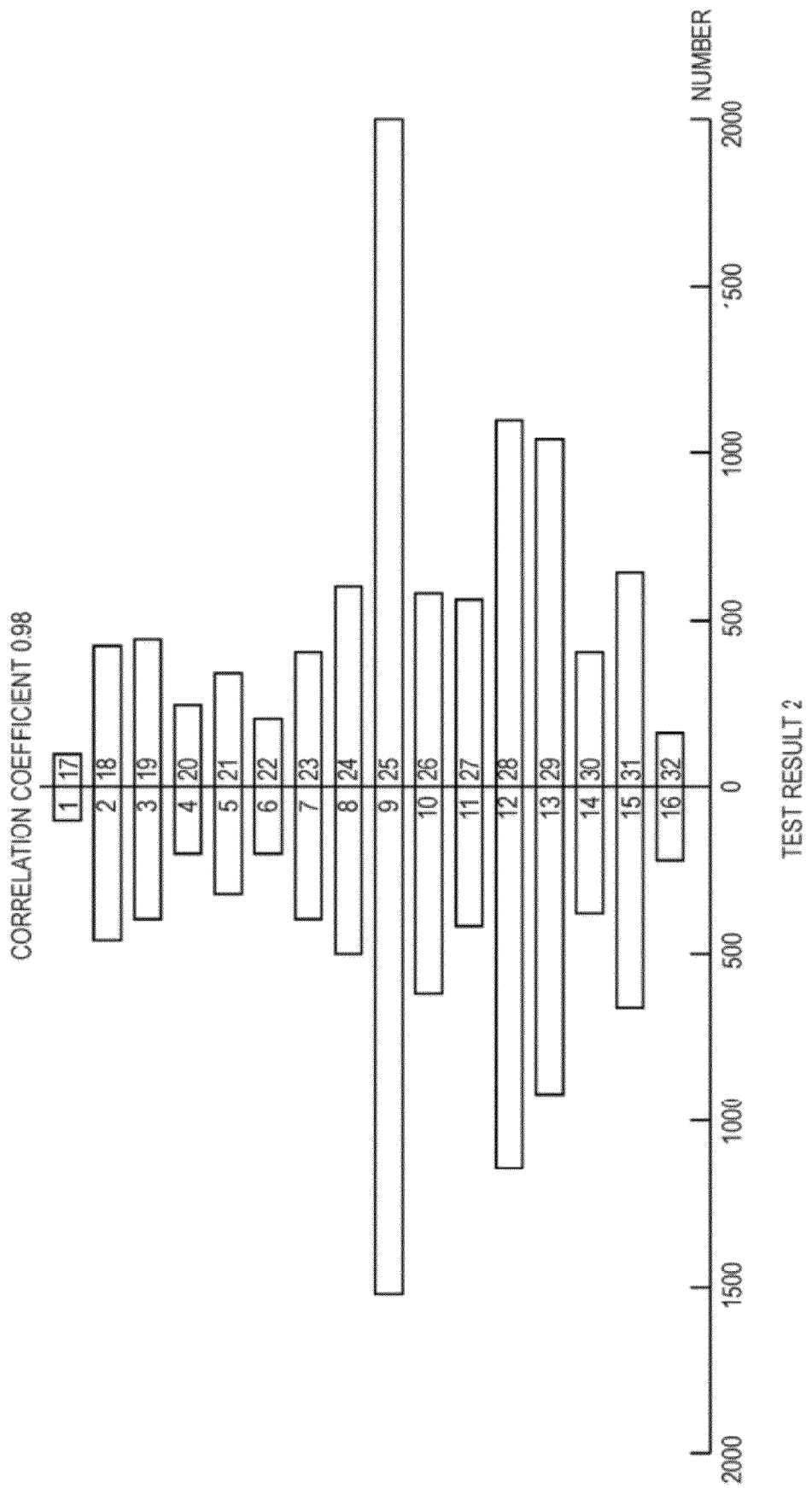

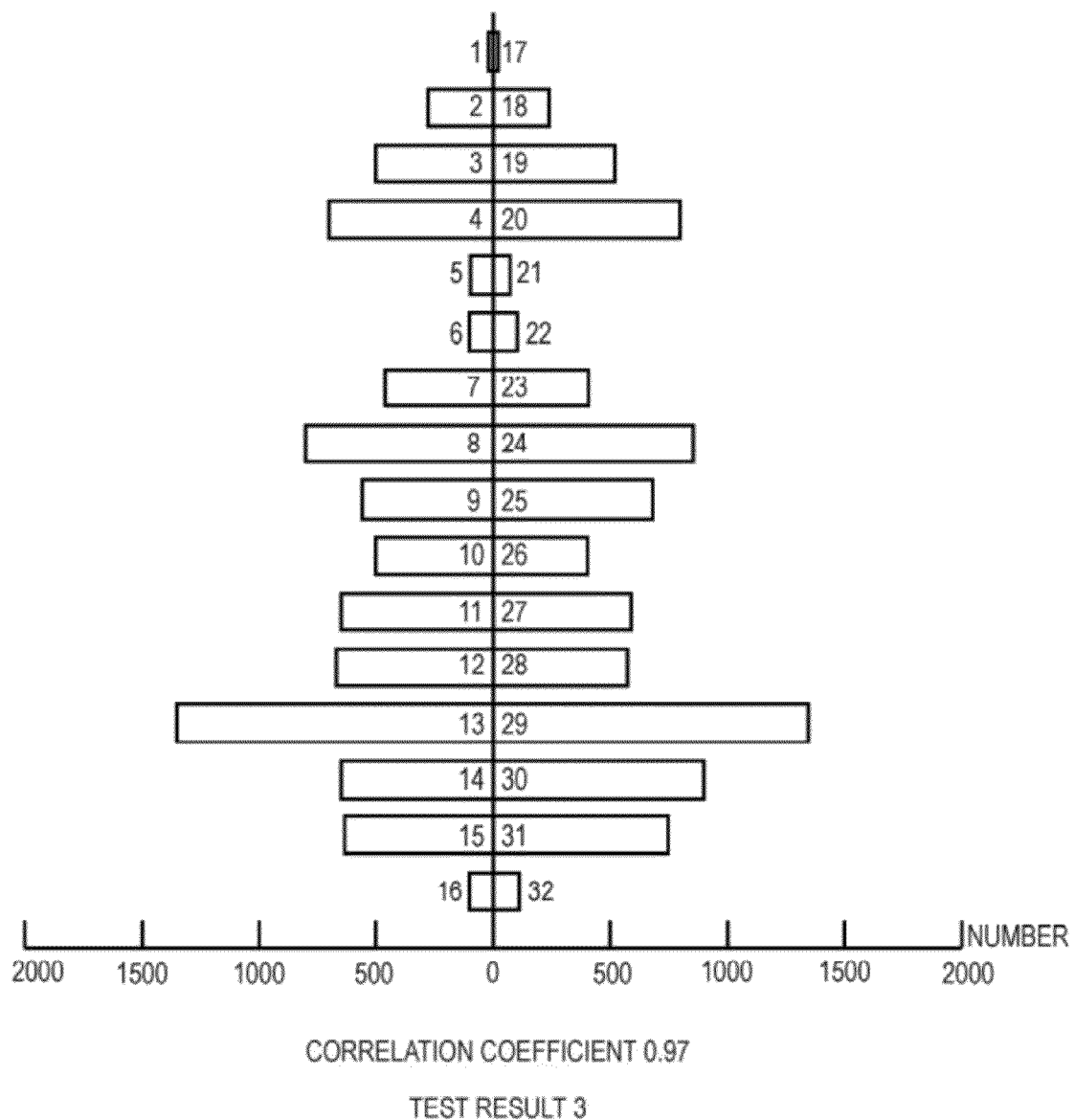

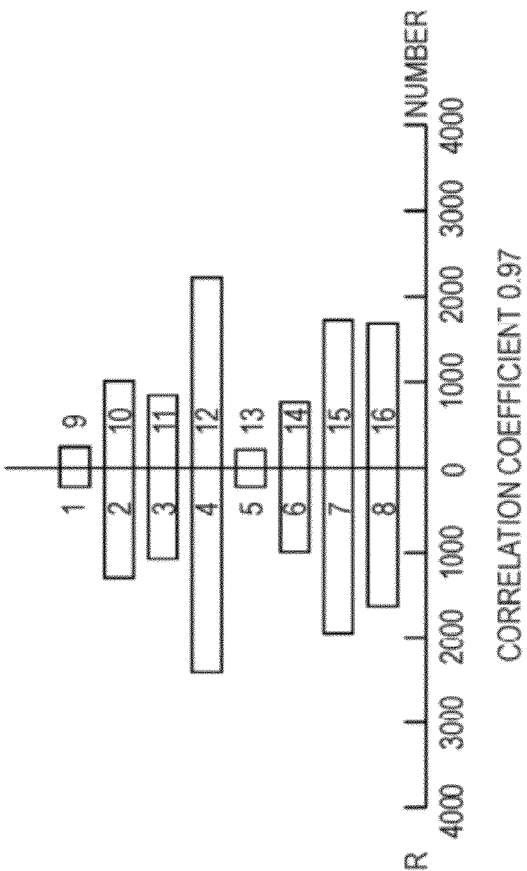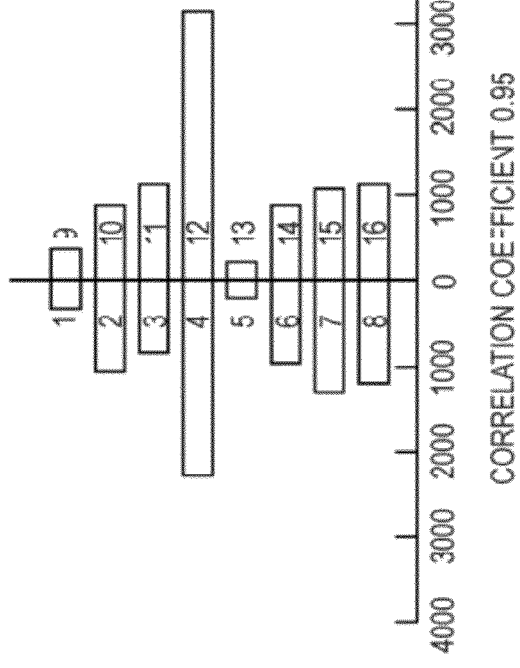

FIG.12

EXPRESSION CHANGE PATTERN WHEN THE NUMBER OF
OBSERVATION POINTS IS 5

| | 1 | 2 | 3 | 4 | | 1 | 2 | 3 | 4 |
|---|---|---|---|---|---|---|---|---|---|
| 1 | + | + | + | + | 9 | − | − | − | − |
| 2 | − | + | + | + | 10 | + | − | − | − |
| 3 | + | − | + | + | 11 | − | + | − | − |
| 4 | + | + | − | + | 12 | − | − | + | − |
| 5 | + | + | + | − | 13 | − | − | − | + |
| 6 | − | − | + | + | 14 | + | + | − | − |
| 7 | − | + | − | + | 15 | + | − | + | − |
| 8 | − | + | + | − | 16 | + | − | − | + |

FUNCTIONAL CONFIGURATION (2) OF CPU FOR PERFORMING GENE CLASSIFYING PROCESS

COMBINATION PATTERN HAVING PAIRS OF TWO OBSERVATION POINTS WHEN THE NUMBER OF OBSERVATION POINTS IS 5

| CLASSIFICATION No. | MAXIMUM, MINIMUM |
|---|---|
| 1 | t1,t2 |
| 2 | t1,t3 |
| 3 | t1,t4 |
| 4 | t1,t5 |
| 5 | t2,t1 |
| 6 | t2,t3 |
| 7 | t2,t4 |
| 8 | t2,t5 |
| 9 | t3,t1 |
| 10 | t3,t2 |
| 11 | t3,t4 |
| 12 | t3,t5 |
| 13 | t4,t1 |
| 14 | t4,t2 |
| 15 | t4,t3 |
| 16 | t4,t5 |
| 17 | t5,t1 |
| 18 | t5,t2 |
| 19 | t5,t3 |
| 20 | t5,t4 |

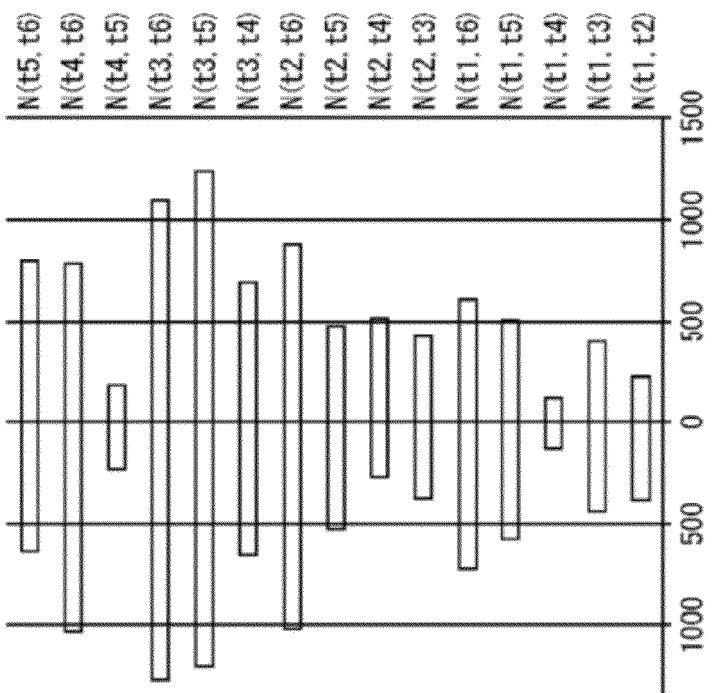
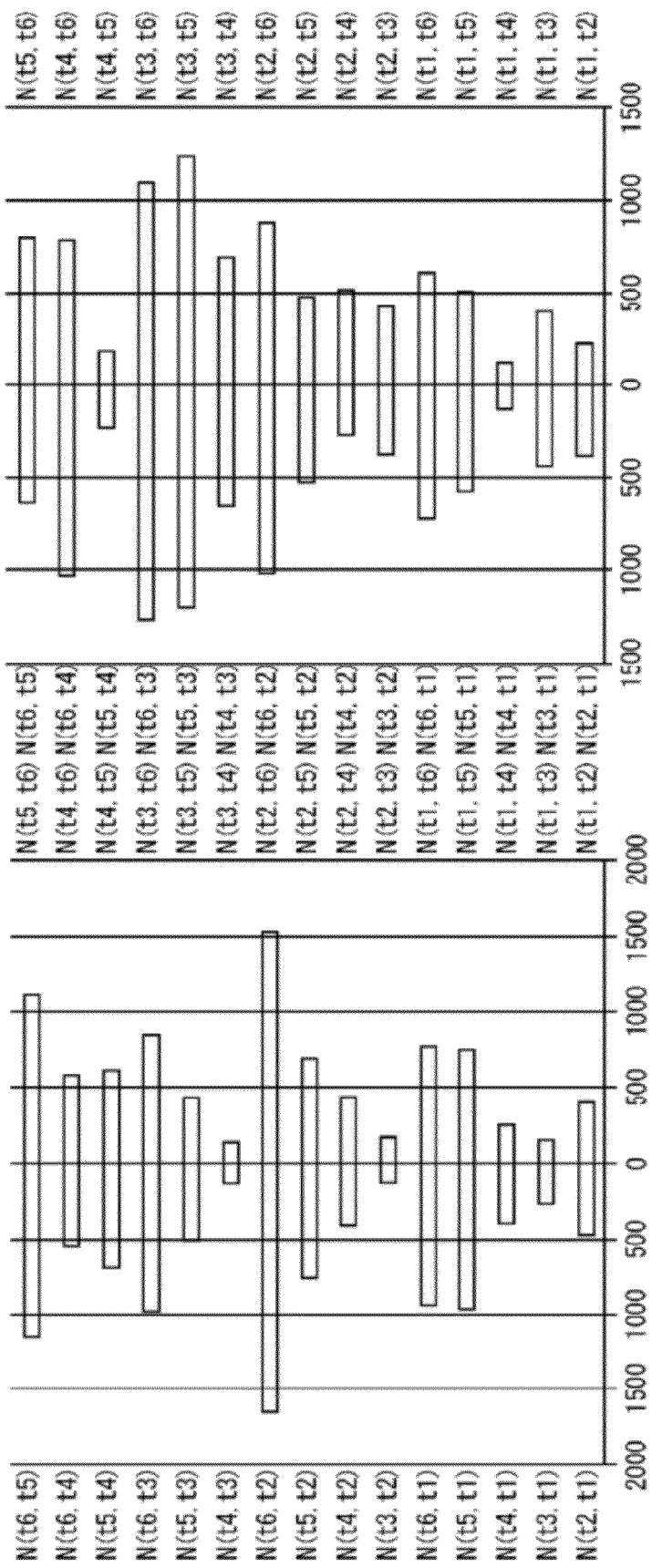
TEST RESULT 5

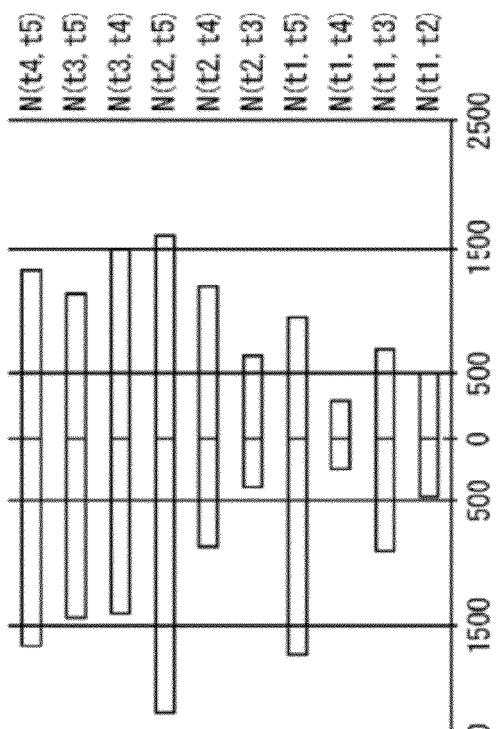
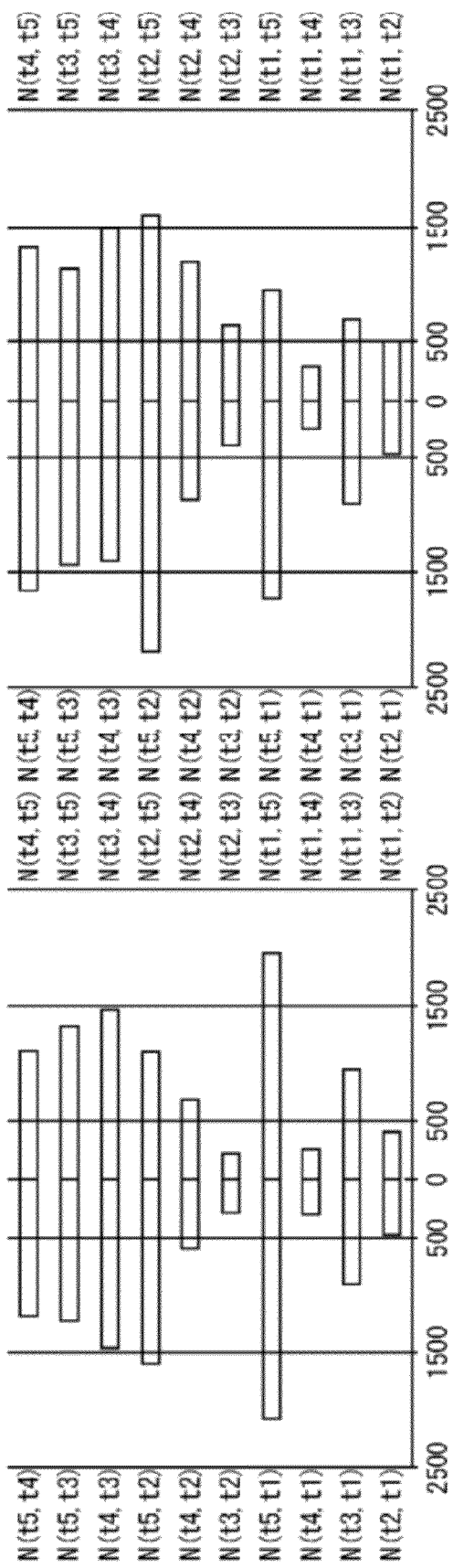
TEST RESULT 6

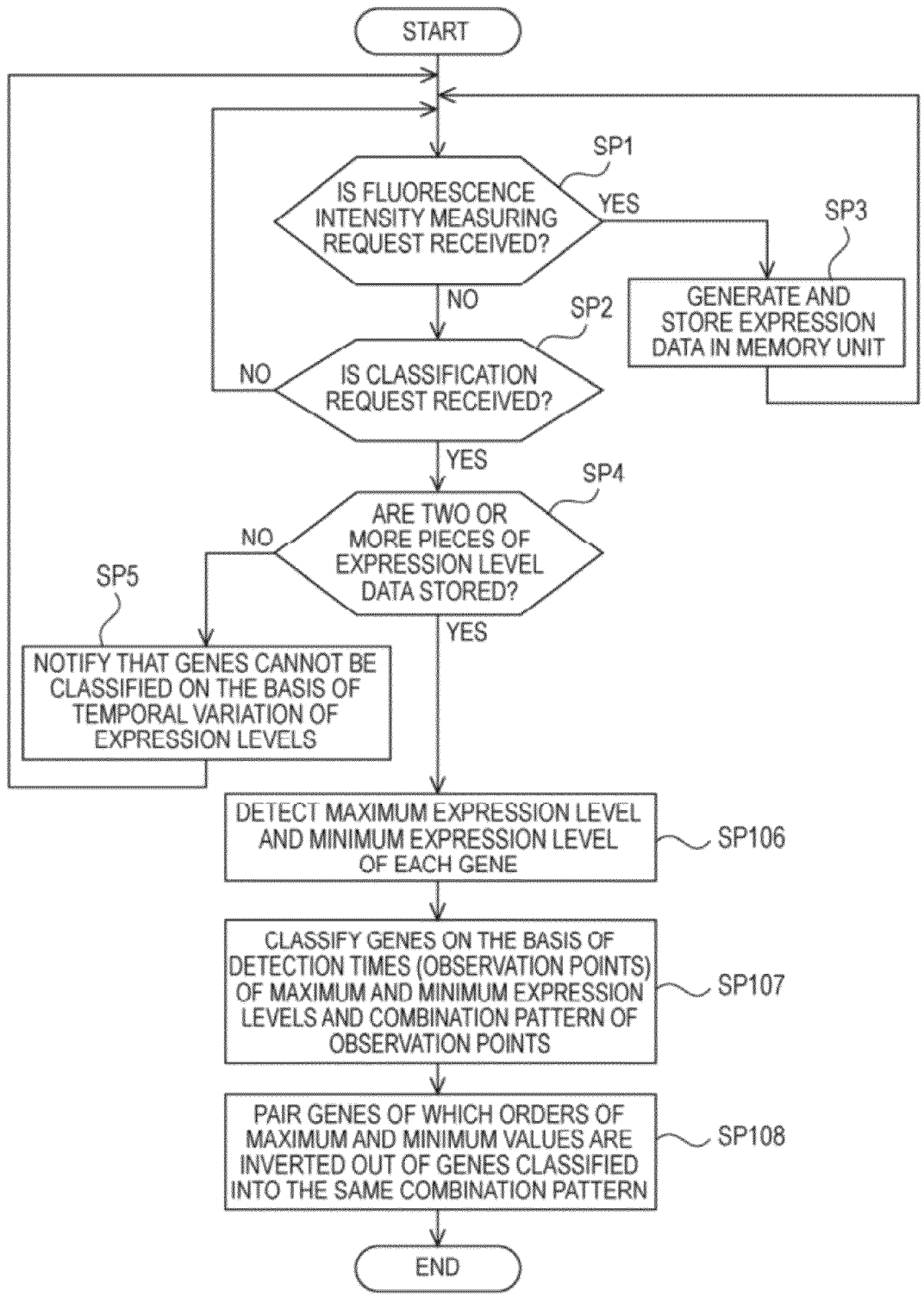

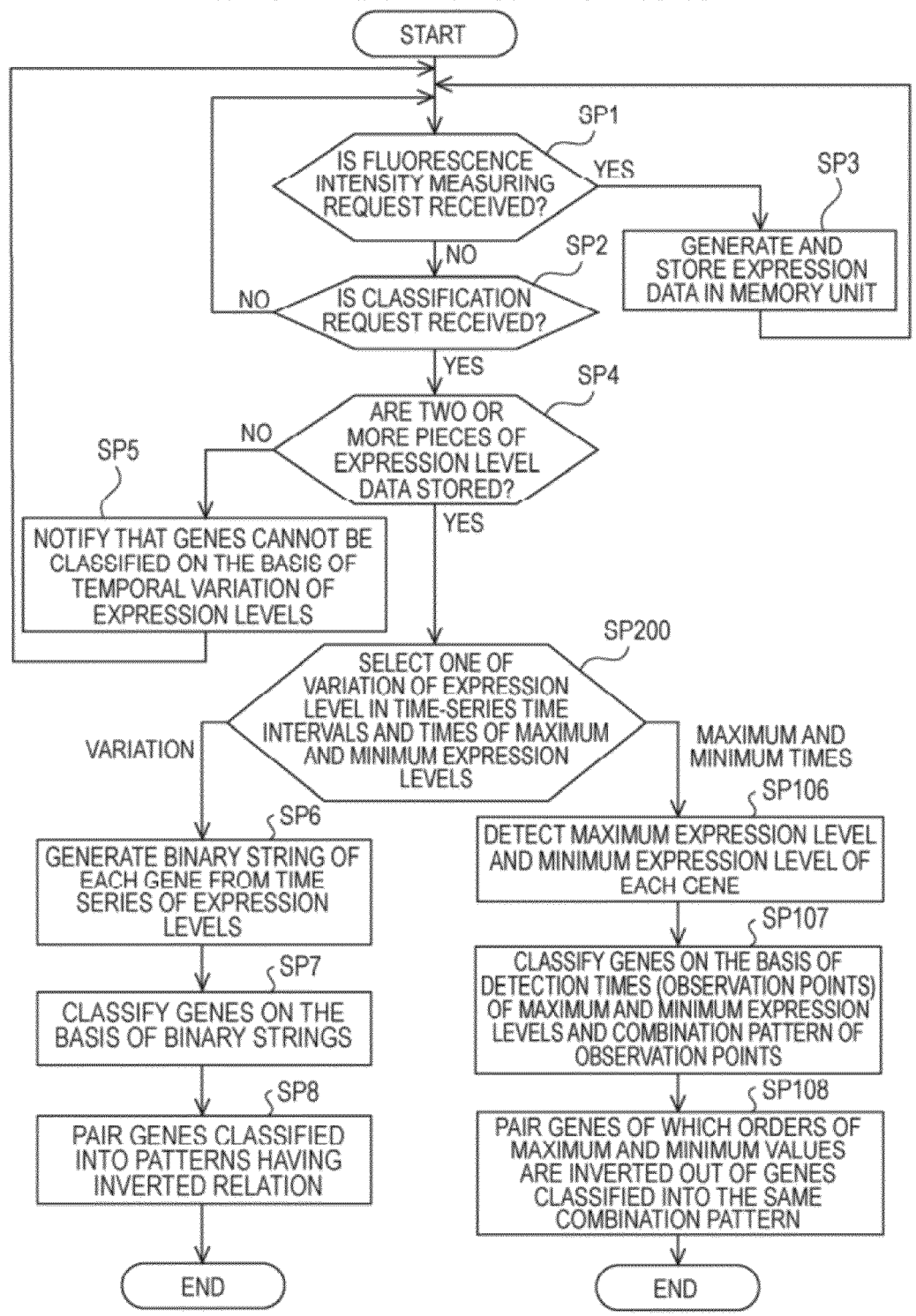

GENE CLASSIFYING METHOD, GENE CLASSIFYING PROGRAM, AND GENE CLASSIFYING DEVICE

CROSS REFERENCES TO RELATED APPLICATIONS

The present application claims priority to Japanese Priority Patent Applications JP 2008-213112 and JP 2008-324244 filed in the Japan Patent Office on Aug. 21, 2008 and Dec. 19, 2008, respectively, the entire contents of which are hereby incorporated by reference.

BACKGROUND

The present disclosure relates to a gene classifying method, a gene classifying program, and a gene classifying device, and more particularly, to a technical field of utilizing a gene expression level obtained using a bioassay bed.

In the past, a technique was known which measures gene expression levels of genes expressed in a sample cell using an amount of complementary strands formed by mRNA extracted from the sample cell or cDNA thereof and nucleic acid probes as an indicator (for example, see JP-A-2008-82876).

The gene expression levels are compared with each other between different cells or different times under different conditions and a difference thereof is extracted and analyzed, thereby exhibiting usefulness thereof. As an aspect of analyzing a gene expression level, however, there is a need for classifying genes on the basis of temporal variations of the gene expression levels.

However, there is currently no criterion for the temporal variations of the gene expression levels used to classify the genes into categories. Even when the criterion exists but two different genes are compared out of several ten thousands of genes, all possible combinations should be compared, which is inefficient.

Thus, it is desirable to provide a gene classifying method, a gene classifying program, and a gene classifying device, which can simply classify genes on the basis of temporal variations of gene expression levels.

SUMMARY

Embodiments are directed to a first gene classifying method, a first gene classifying program, a first gene classifying device, a second gene classifying method, a second gene classifying program, and a second gene classifying device with which the above-mentioned problems can be solved.

The first gene classifying method of one embodiment includes: acquiring expression levels of a plurality of genes at a plurality of observation points; generating a binary string by taking the positive or negative difference in the expression level in a temporal passage direction of the observation points for each gene; and classifying the genes on the basis of all positive and negative patterns that the binary strings can have and the generated binary strings.

The first gene classifying program of one embodiment enables a computer to perform: acquiring expression levels of a plurality of genes at a plurality of observation points; generating a binary string by taking the positive or negative difference in the expression level in a temporal passage direction of the observation points for each gene; and classifying the genes on the basis of all the positive and negative patterns that the binary strings can have and the generated binary strings.

The first gene classifying device of one embodiment includes: acquiring means for acquiring expression levels of a plurality of genes at a plurality of observation points; generating means for generating a binary string by taking the positive or negative difference in the expression level in a temporal passage direction of the observation points for each gene; and classifying the genes on the basis of all the positive and negative patterns that the binary strings can have and the binary strings generated by the generating means.

The second gene classifying method of one embodiment includes: acquiring expression levels of a plurality of genes at a plurality of observation points; detecting the maximum expression level and the minimum expression level of each gene; and classifying the genes on the basis of combination patterns including pairs of two observation points and the observation points of the detected maximum and minimum expression levels.

The second gene classifying program of one embodiment enables a computer to perform: acquiring expression levels of a plurality of genes at a plurality of observation points; detecting the maximum expression level and the minimum expression level of each gene; and classifying the genes on the basis of combination patterns including pairs of two observation points and the observation points of the detected maximum and minimum expression levels.

The second gene classifying device of one embodiment includes: acquiring means for acquiring expression levels of a plurality of genes at a plurality of observation points; detecting means for detecting the maximum expression level and the minimum expression level of each gene; and classifying means for classifying the genes on the basis of combination patterns including pairs of two observation points and the observation points of the maximum and minimum expression levels detected by the detecting means.

According to the first gene classifying method, the first gene classifying program, and the first gene classifying device of the embodiments, by converting the expression levels of the observation points into strings of binary values (binary strings) based on the variations of the expression levels "increasing" or "decreasing" depending on the time change of the observation points, it is possible to necessarily obtain patterns (plus and minus patterns) that the binary strings can have. Therefore, according to embodiments, it is possible to simply pattern the genes on the basis of the temporal variation of the expression levels.

In addition, compared with the case where the genes are classified into patterns on the basis of all the combinations that two different genes out of several tens of thousands of genes can have using the expression levels at the observation points without conversion into the strings of binary values (binary strings), it is possible to further greatly reduce the time (load) required for the classification.

According to the second gene classifying method, the second gene classifying program, and the second gene classifying device, by only acquiring the expression levels of a plurality of genes at a plurality of observation points, it is possible to necessarily obtain the combination patterns having pairs of two observation points. Therefore, according to the embodiments of the invention, it is possible to simply pattern the genes on the basis of the time when the gene expression levels reach the maximum or the minimum.

In addition, unlike the first gene classifying method, the first gene classifying program, and the first gene classifying device, since the genes are classified into the combination patterns necessarily obtained on the basis of the number of observations without conversion into the binary strings, it is possible to greatly reduce the time (load) required for the classification. However, the reduction of the process time is not a factor for determining the superiority and inferiority of the classification ability.

Additional features and advantages are described herein, and will be apparent from the following Detailed Description and the figures.

BRIEF DESCRIPTION OF THE FIGURES

FIG. 7 is a diagram schematically illustrating an expression change pattern when the number of observation points is 6.

FIG. 9 is a graph illustrating test result 2.

FIG. 10 is a graph illustrating test result 3.

FIGS. 11A and 11B are graphs illustrating test result 4.

FIG. 12 is a diagram schematically illustrating the expression change pattern when the number of observation points is 5.

FIGS. 16A and 16B are graphs illustrating test result 5.

FIGS. 17A and 17B are graphs illustrating test result 6.

FIG. 18 is a flowchart illustrating a flow of a second gene classifying process.

FIG. 19 is a flowchart illustrating a flow of a third gene classifying process.

DETAILED DESCRIPTION

Figure 1:
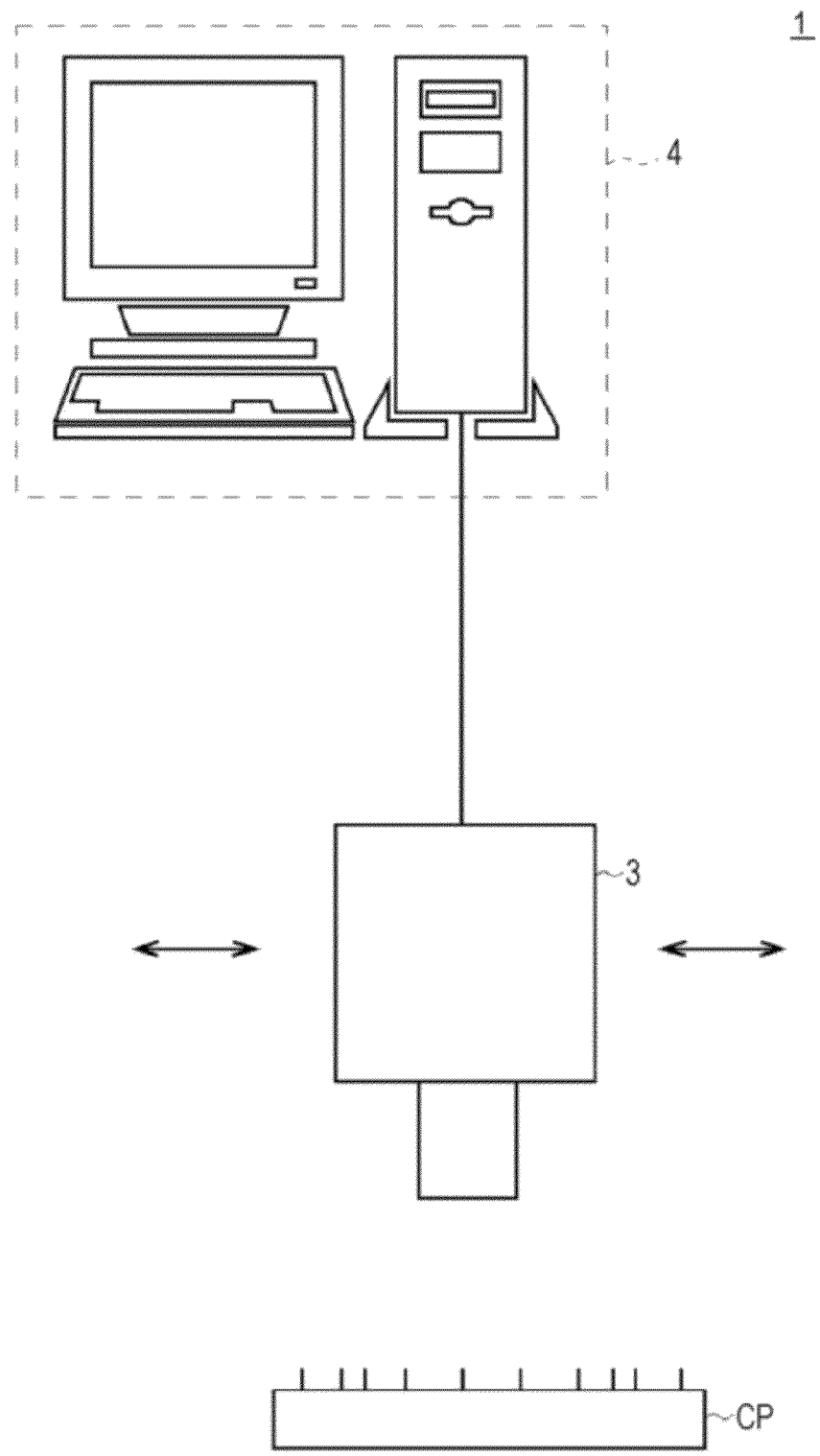
FIG. 1 is a diagram schematically illustrating the entire configuration of a gene analysis system according to an embodiment.

Hereinafter, embodiments will be described. The description will be made in the following order.
1. Configuration of Gene Analysis System
2. Circuit Configuration of Gene Classifying Device
3. Gene Classifying Process
3-1. First Gene Classifying Process
3-1-1. Functional Configuration
3-1-2. Flow of Gene Classifying Process
3-1-3. Advantage and others
3-2. Second Gene Classifying Process
3-2-1. Functional Configuration
3-2-2. Flow of Gene Classifying Process
3-2-3. Advantage and others
4. Other Embodiments 1. Configuration of Gene Analysis System FIG. 1 shows the entire configuration of a gene analysis system 1 according to an embodiment. The gene analysis system 1 includes a fluorescence intensity measuring device 3 and a gene classifying device 4.

The fluorescence intensity measuring device 3 includes a measurement stage and a nucleic acid tip CP is set on the measurement stage. The nucleic acid tip CP is a bed on which nucleic acid probes corresponding to genes in a target cell are arranged.

Figure 2:
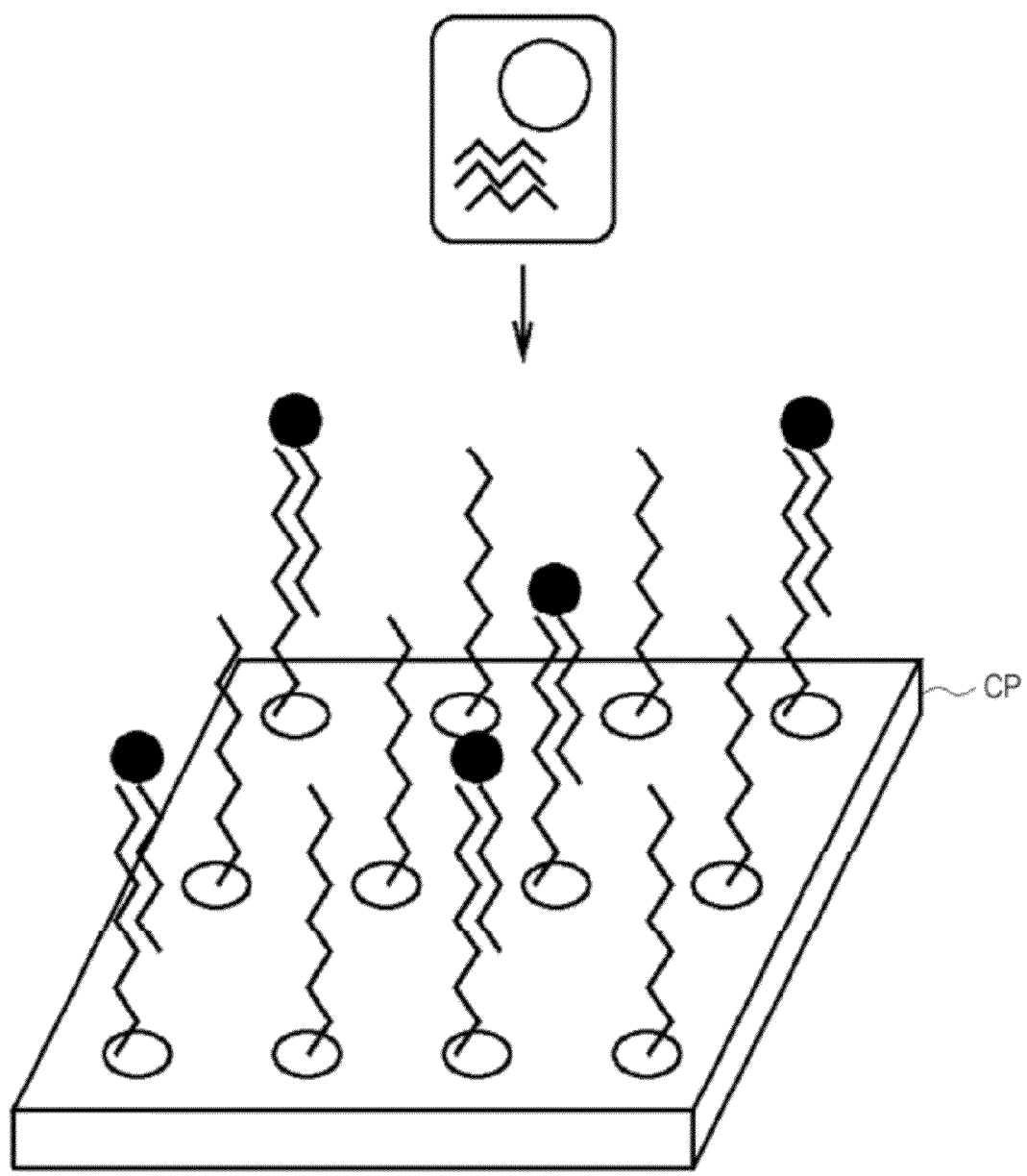
FIG. 2 is a diagram schematically illustrating hybridization in a nucleic acid tip.

In the nucleic acid tip CP, for example, as shown in FIG. 2, target nucleic acids (portions indicated by short waved lines) which are extracted from a target cell and to which labeled substances (portions indicated by black circles) are added are assigned to the nucleic acid probes (portions indicated by long waved lines) and a complementary strand forming reaction (hereinafter, referred to as "hybridization") is performed thereon.

The nucleic acid probes are generally designed as nucleotide fragments (hereinafter, referred to as "probe set") which are paired in plural base sequence portions specific to a specific gene, not as nucleotides paired in the overall base sequences in the specific gene. Controls of the probe sets are also designed. The probe sets and the controls are arranged in a predetermined region assigned to the nucleic acid tip CP. Specifically, DNA (Deoxyribonucleic acid) fragments, cDNA (Complementary DNA) fragments, or PNA (Peptide Nucleic Acid) of about 18 to 60 [mer] are used as the probe fragments.

On the other hand, a target nucleic acid is a single-strand nucleotide to be hybridized with a nucleic acid probe. In general, mRNA (including pre-mRNA) or its fragment itself is not used as the target nucleic acid, but the resultant into which the mRNA or its fragment is transformed with reverse transcriptase is used.

The labeled substance is generally a fluorescent dye such as biotin or FITC (Fluorescein Isothiocyanate). However, the labeled substance is not limited to the fluorescent dye but may employ, for example, a radioactive isotope.

The fluorescence intensity measuring device 3 (see FIG. 1) applies exciting light from the labeled substance added to the target nucleic acid to the nucleic acid tip CP set on the measurement stage, when a measurement instruction is given. When the nucleic acid probes being arranged in the nucleic acid tip CP to correspond to genes form complementary strands with the target nucleic acids, the labeled substance added to the target nucleic acids emits light with the exciting light. The emission intensity is associated with the amount of complementary strands formed by the target nucleic acids and the nucleic acid probes. That is, as the amount of the target nucleic acids forming the complementary strands with the nucleic acid probes increases, the emission intensity also increases.

The fluorescence intensity measuring device 3 measures the emission intensity from the nucleic acid probes and the controls after applying the exciting light thereto and outputs data indicating the measured emission intensity (hereinafter, referred to as "fluorescence intensity data").

Figure 3:
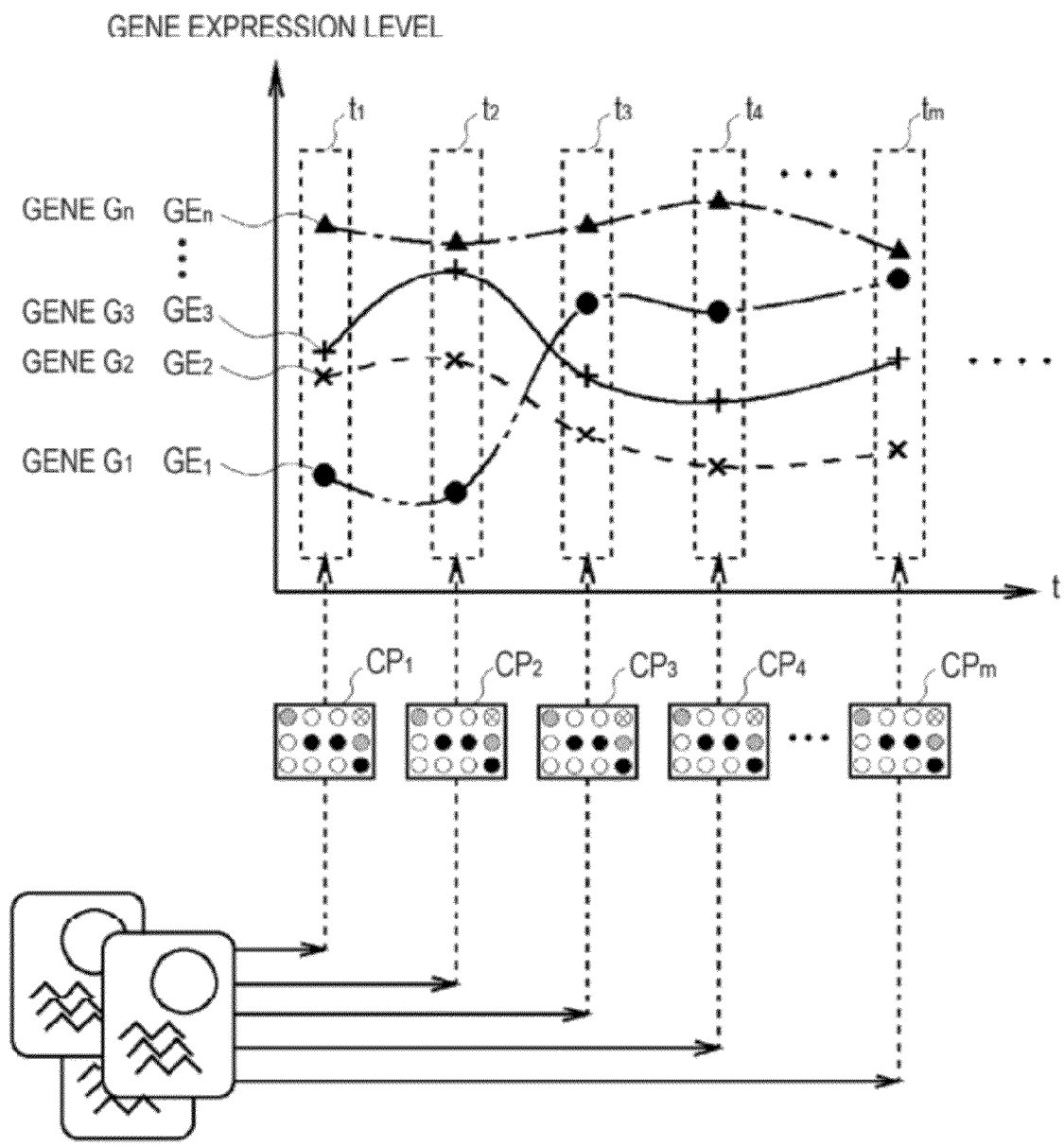
FIG. 3 is a diagram schematically illustrating acquisition of gene expression levels in a target cell at observation points.

For example, as shown in FIG. 3, the gene classifying device 4 acquires expression levels $GE_n$ of genes $G_n$ (where n is a natural number) in a target cell at each observation point $t_m$ (where m is a natural number) from the hybridization result (fluorescence intensity data) of the target nucleic acids extracted from continuously-cultivated target cells at each predetermined observation time and the nucleic acid probes arranged in the nucleic acid tip CP.

Then, the gene classifying device 4 classifies the genes $G_n$ on the basis of the temporal variations of the expression levels $GE_n$.

2. Circuit Configuration of Gene Classifying Device

Figure 4:
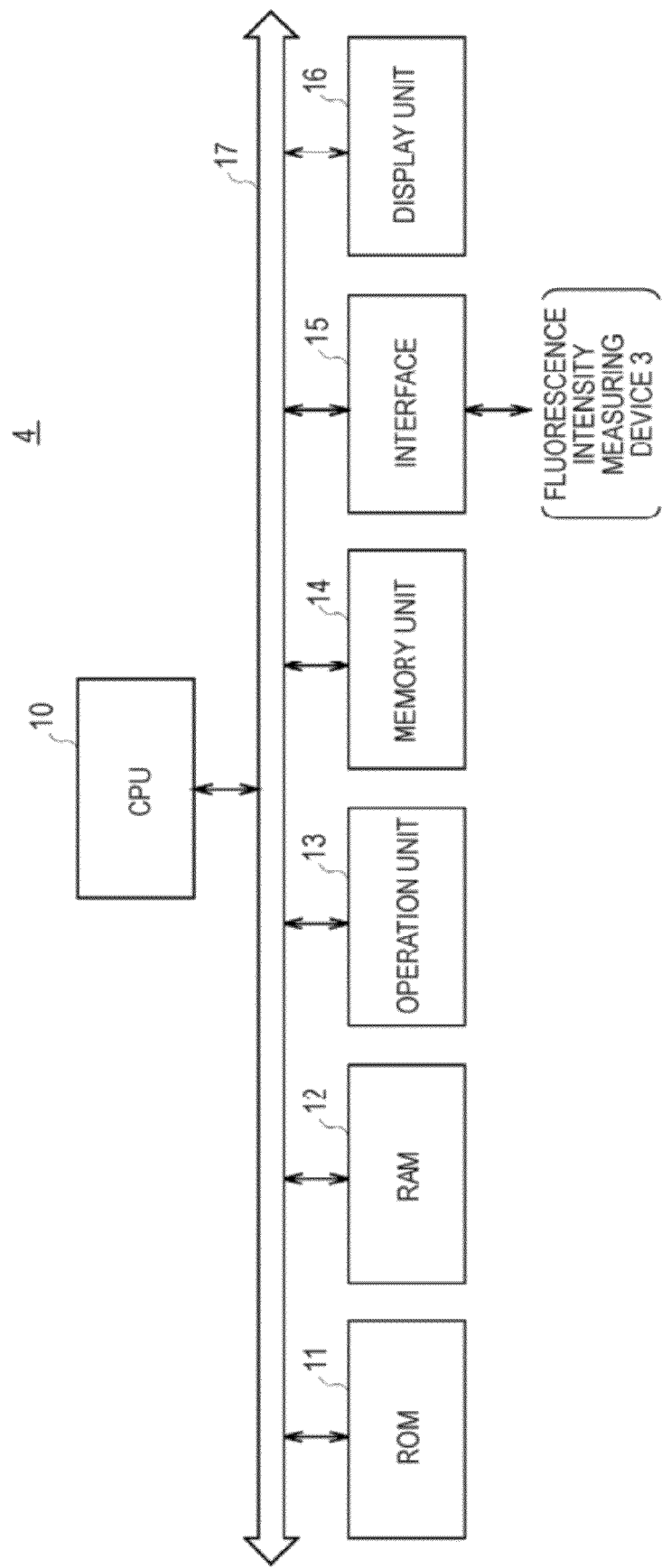
FIG. 4 is a block diagram illustrating the configuration of a gene classifying device.

The configuration of the gene classifying device 4 will be described now. As shown in FIG. 4, the gene classifying device 4 is constructed by connecting a variety of hardware to a CPU (Central Processing Unit) 10 controlling the entire gene classifying device 4.

Specifically, for example, a ROM (Read Only Memory) 11, a RAM (Random Access Memory) 12 serving as a work area of the CPU 10, an operation unit 13, a memory unit 14, an interface 15, and a display unit 16 are connected via a bus 17.

A program (hereinafter, also referred to as "gene classifying program") for assaying a gene expression level is stored in the ROM 11. The interface 15 can transmit and receive data to and from the fluorescence intensity measuring device 3 in a wired or wireless manner.

When the gene classifying program stored in the ROM 11 is developed in the RAM 12, the CPU 10 properly controls the memory unit 14, the interface 15, and the display unit 16 on the basis of the gene classifying program to perform a gene classifying process.

3. Gene Classifying Process

The gene classifying process will be specifically described now with reference to two examples.

3-1. First Gene Classifying Process

3-1-1. Functional Configuration

Figure 5:
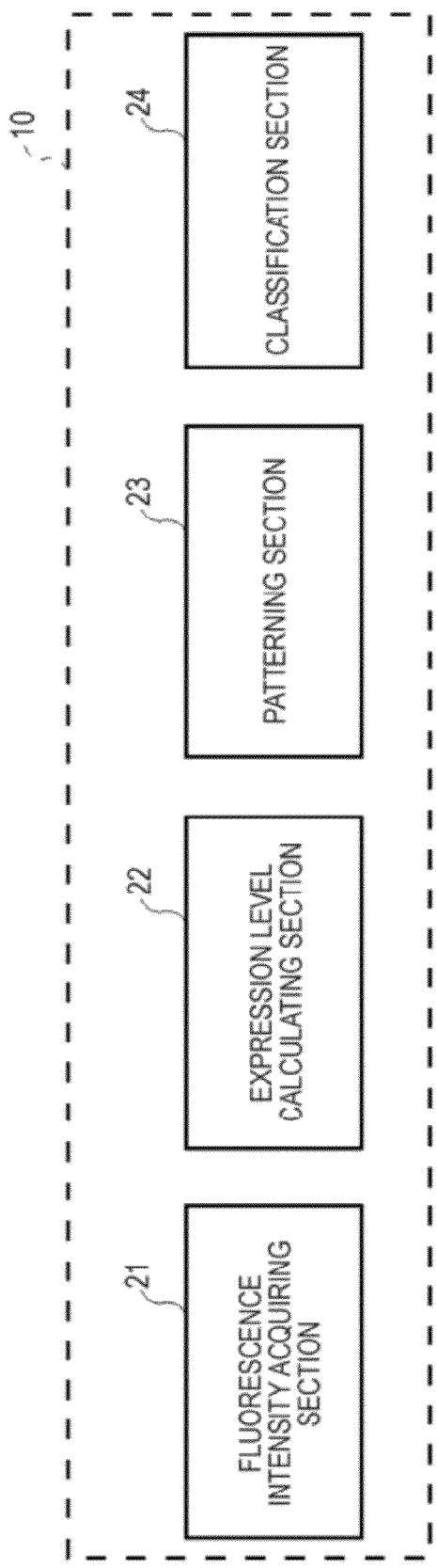
FIG. 5 is a block diagram illustrating the functional configuration (1) of a CPU for performing a gene classifying process.

In the first gene classifying process, as shown in FIG. 5, the CPU 10 serves as a fluorescence intensity acquiring section 21, an expression level calculating section 22, a binarization section 23, and a classification section 24.

The fluorescence intensity acquiring section 21 waits for a fluorescence intensity measurement request on a nucleic acid tip CP from the operation unit 13, and requests the fluorescence intensity measuring device 3, connected to the interface 15, for the measurement through the interface 15 when receiving the measurement request.

The fluorescence intensity acquiring section 21 generates, for example, an acquisition date and an acquisition number as identification data of the nucleic acid tip CP (hereinafter, referred to as "tip identification data") when acquiring the fluorescence intensity data from the fluorescence intensity measuring device 3 in response to the measurement request.

When the fluorescence intensity acquiring section 21 acquires the fluorescence intensity data, the expression level calculating section 22 calculates the gene expression levels of each probe set on the basis of the fluorescence intensity data, correlates data (hereinafter, referred to as "expression level data") representing the calculated expression levels of each probe set with the tip identification data, and stores the resultant data in the memory unit 14.

The gene expression level is an estimated level representing a gene expressed in the target cell and, for example, the level is calculated as a ratio of emission intensity from the emission intensity correlated with the amount of complementary strands formed by the target nucleic acids and the nucleic acid probes.

In this embodiment, the gene expression level is calculated by the use of version 5 of data analysis software called MAS (Micro Array Suite) made by Affymetrix Inc.

Here, the MAS5 will be described in brief paying attention to a single probe set. In the MAS5, (1) a local physical influence (background) is excluded from the emission intensity of each probe fragment in the probe set, (2) the emission intensity of each probe fragment (referred to as "perfect match probe") is properly corrected depending on a difference between the probe fragment and the corresponding fragment control (referred to as "mismatch probe"), and (3) the emission intensity of each probe fragment (referred to as "perfect match probe") is calculated as a gene expression level by algebraic transformation.

In the MAS5, normalization of scaling different probe sets so as to have the same average fluorescence intensity as a reference probe set is made. Specifically, the process details of the MAS5 can be referred to "Micro Array Data Analysis for Combined Genomics," written by I. S. Kohane/A. T. Kho/ A. J. Butte, and Hosida Arihito and published by Springer Japan, p. 58-74.

The binarization section 23 waits for a gene classification request and recognizes the gene expression level $GE_n$ at an observation point $t_m$ on the basis of the tip identification data and the expression level data stored in the memory unit 14 when receiving the classification request.

Here, when only the gene expression level $GE_1$ at a single observation point $t_1$ is recognized, it means that information on the temporal variation of the gene expression level in the target cell is not acquired and thus the genes cannot be classified on the basis of the temporal variation of the gene expression level. In this case, the binarization section 23 notifies this fact, for example, using the display unit 16.

On the contrary, when the gene expression levels $GE_n$ at two or more observation points $t_m$ are recognized, the binarization section 23 generates a binary string (hereinafter, referred to as "expression level binary string") by taking the positive or negative difference in gene expression level $GE_n$ in the temporal passage direction of the observation points $t_m$.

Figure 6:
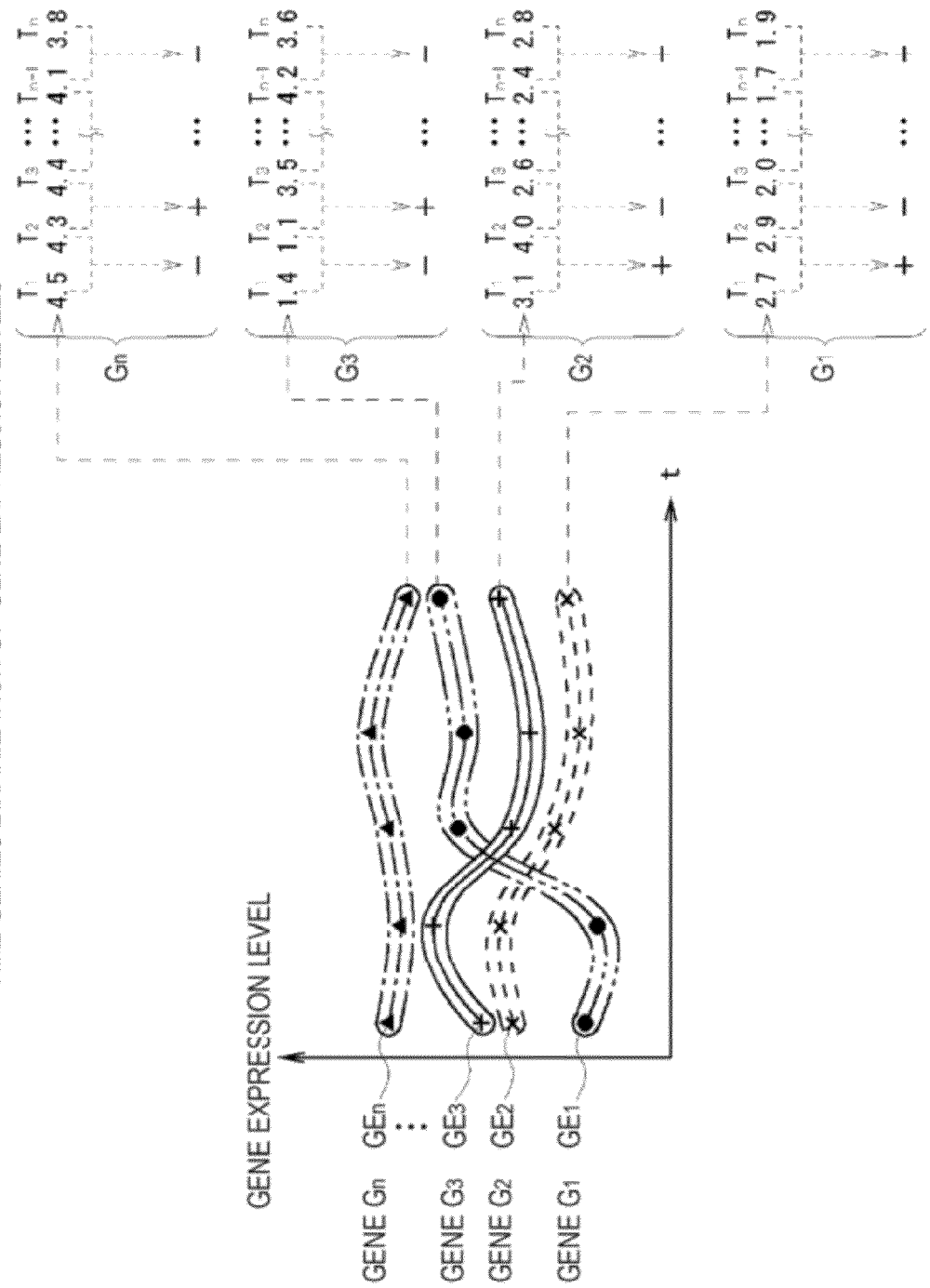
FIG. 6 is a diagram schematically illustrating time-series binarization of gene expression levels.

In the example shown in FIG. 3, as shown in FIG. 6, the expression level binary strings are generated from the time-series gene expression levels $GE_n$ by setting the binary string to negative (minus) when the difference in the temporal passage direction of the gene expression levels $GE_n$ in the interval between the observation points (temporally adjacent) is less than 0 and setting the binary string to positive (plus) when the difference is greater than 0. The values of the gene expression levels $GE_n$ in FIG. 6 are expressed for the purpose of convenience and are not actual numerical values.

The total number of different plus and minus patterns (hereinafter, referred to as "expression change pattern") that the expression level binary strings can have is calculated by using a numerical value obtained by subtracting "1" from the number of observation points $t_m$ as an exponent and setting 2 as the minimum value.

Specifically, for example, when the number of observation points $t_m$ is 6, the expression change patterns have $2^5$ types as shown in FIG. 6. In FIG. 6, for the purpose of convenience, the expression change patterns having a symmetric property are shown on the left and right sides.

The classification section 24 recognizes $2^{(m-1)}$ expression change patterns from the number of observation points $t_m$ and classifies the genes $G_n$ on the basis of the expression change patterns and the expression level binary strings generated by the binarization section 23.

Specifically, for example, identifiers such as numbers are assigned to the $2^{(m-1)}$ expression change patterns and the identifier of the expression change pattern indicated by the expression level binary strings of each gene $G_n$ is added to the corresponding expression level data.

In addition, the classification section 24 pairs the genes classified into the expression change patterns having an inverted relation out of the genes $G_n$ classified into plural expression change patterns.

For example, in the expression change patterns shown in FIG. 7, when two genes $G_2$ and $G_{38}$ classified into "1" exist and two genes $G_{12}$ and $G_{17}$ classified into "17" exist, data is generated which states that four pairs of $G_2$ and $G_{12}$, $G_2$ and $G_{17}$, $G_{38}$ and $G_{12}$, and $G_{38}$ and $G_{17}$ are gene pairs having the pattern of "1" (that is, "+++++") and the pattern of "17" (that is, "-----").

Figure 8B:
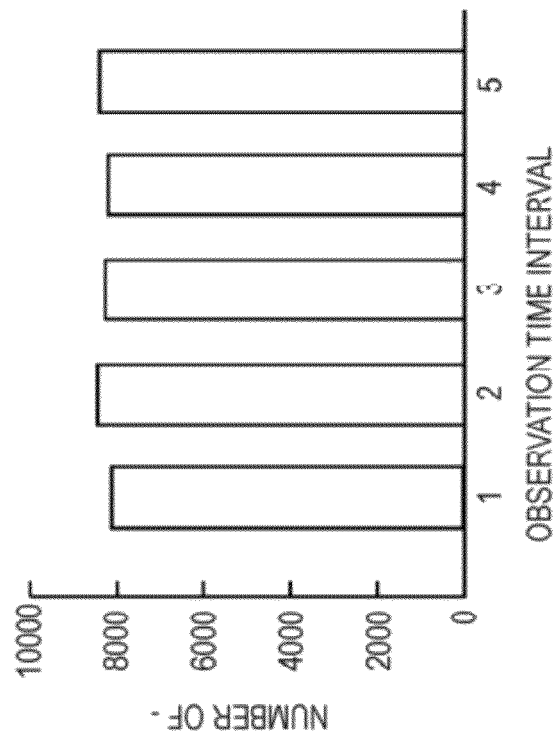
FIGS. 8A and 8B are graphs illustrating test result 1.
Figure 8A:
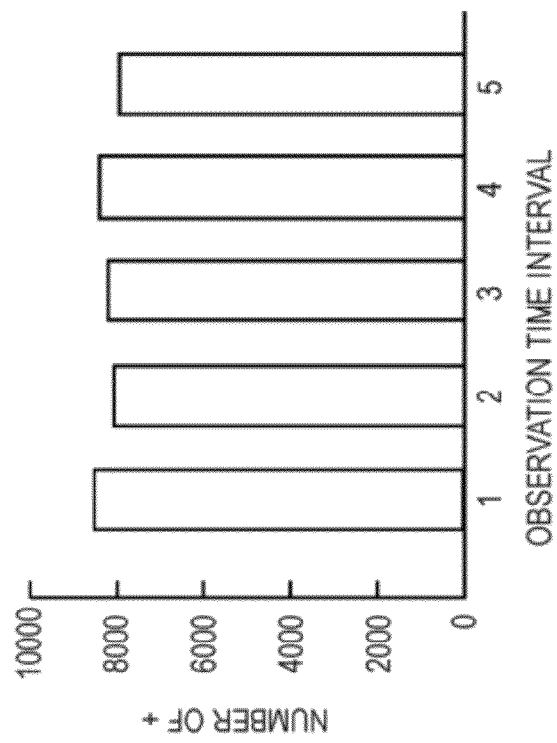

Test results are shown in FIGS. 8A and 8B. FIGS. 8A and 8B show the number of genes (FIG. 8A) having a positive change in the observation point interval at the observation points $t_m$ and the number of genes (FIG. 8B) having a negative change when asbestos is given as a stimulus to A549 cell using E-GEOD-6013 as a sample.

The observation points in this test are time points of 0, 1, 6, 24, and 48 [hours] and 7 [days]. Therefore, "1" in the horizontal axis represents an interval between 0 and 1 hour, "2" represents an interval between 1 to 6 hours, and "5" represents an interval between 48 hours and 7 days. The number of genes in this test is 16896.

As shown in FIGS. 8A and 8B, the number of genes having a positive change and the number of genes having a negative change are equal in the respective observation point intervals. In the test result shown in FIGS. 8A and 8B, the number of genes having a positive change is 50.1 [%] of the total number of genes and the number of genes having a negative change is 49.9 [%] of the total number of genes.

The test result obtained by classifying the genes into the expression change patterns shown in FIG. 7 under the same condition as shown in FIGS. 8A and 8B is shown in FIG. 9. As shown in FIG. 9, the numbers of expression change patterns having a symmetric property are equal and the correlation of the distribution is "0.98".

Regarding the expression level binary strings of the genes $G_n$, it was confirmed from the test results shown in FIGS. 8A and 8B and FIG. 9 that the number of genes having a positive change and the number of genes having a negative change have a symmetric property and the numbers of genes in the patterns having inverted plus and minus changes have a symmetric property.

When a first symmetric property that the number of genes having a positive change and the number of genes having a negative change are symmetric is established, a second symmetric property that the numbers of genes in the patterns having inverted plus and minus changes are symmetric can be also proved.

That is, the $2^{(m-1)}$ binary strings (expression level binary strings) can be defined by the following expression.

$$\{A1, A2, \ldots, Am\}, (Ak=\{+, -\}, 1 \leq k \leq m) \qquad (1)$$

Since the second symmetric property should be proved, the following expression is established.

$$\text{Number of } \{A1, A2, \ldots, Am\} = \text{Number of } \{\overline{A1}, \overline{A2}, \ldots, \overline{Am}\} \text{ provided that } Ak=+, \text{ then } \overline{Ak}=- \qquad (2)$$

The mathematical induction is used as the proving method. That is, the number of elements is made to increase by 1 from 1 and it is proved that the second symmetric property is established with the number of elements.

First, as a first step, when the number of elements is 1 (that is, m=1), the following expression is obtained and thus the first symmetric property and the second symmetric property are equal to each other. Therefore, things having the first symmetric property can be said to have the second symmetric property.

$$\text{Number of } \{A1\} = \text{Number of } \{\overline{A1}\} \qquad (3)$$

As a second step, when the number of elements is 2 (that is, m=2), the first symmetric property (that the number of genes having a positive change and the number of genes having a negative change are symmetric) can be changed to "the numbers of binary strings in which the sequences of signs of the final element and the previous element are inverted are equal." That is, the number of binary strings in which the final element is plus and the previous element is minus is equal to the number of binary strings in which the final element is minus and the previous element is plus, or the number of binary strings in which the final element is plus and the previous element is plus is equal to the number of binary strings in which the final element is minus and the previous element is minus. Therefore, when the number of elements is 2, things having the first symmetric property can be said to have the second symmetric property.

As a third step, when the number of elements is t+1 (that is, m=t+1) and it is assumed that the second symmetric property is established when the number of elements m is equal to t, the following expression is obtained. Since the number of arrangement types of signs is $2^t$ in m=t, the number of types of Expression (4) is $2^{t-1}$.

$$\text{Number of } \{A1, A2, \ldots, At\} = \text{Number of } \{\overline{A1}, \overline{A2}, \ldots, \overline{At}\} \qquad (4)$$

By considering the arrangement of signs in m=t+1 and using the idea that "the numbers of binary strings in which the arrangements of signs of the final element and the previous element thereof are inverted are equal," which is used in the second step, the numbers of binary strings in which the arrangements of signs in m=1 and m=t+1 are inverted are equal to each other.

Since the number of types of binary strings in which the arrangements of signs in m=t and m=t+1 are equal is $2^{t-1}$, the total number of types becomes the total number of binary strings in which the arrangements of signs in m=t and m=t+1 are equal and is represented by X.

On the other hand, since the number of types of binary strings in which the arrangements of signs in m=t and m=t+1 are inverted is $2^{t-1}$, the total number of types becomes the total number of binary strings in which the arrangements of signs in m=t and m=t+1 are inverted and is represented by Y. X and Y are equal to each other.

The second symmetric property is established when the number of elements is equal to t. Accordingly, the number of binary strings in which the arrangements of signs in m=t and m=t+1 are inverted out of $2^{t-1}$ types of binary strings is equal. Therefore, the second symmetric property is established when the number of elements m is equal to t+1. That is, Expression (2) is established.

As proved above, the arrangement of the expression level binary strings having the first symmetric property cannot be said to have the second symmetric property in the same number or tendency as actual data, but an arrangement having the first symmetric property can be said to have the second symmetric property.

Test results for the second symmetric property other than the test result shown in FIG. 9 are shown in FIG. 10 and FIGS. 11A and 11B. In FIG. 10, the genes are classified into the expression change patterns shown in FIG. 7, where the conditions other than the condition that asbestos is not applied as a stimulus are the same as shown in FIG. 9. In this case, the number of genes in FIG. 10 is 16453.

On the other hand, FIG. 11A shows the classifying of the genes having a change in the observation point interval at the observation points $t_m$ into the expression change patterns when asbestos is applied as a stimulus to Beas2A cell using E-GEOD-6013 as a sample and FIG. 11B shows the classifying of the genes having a change in the observation point interval at the observation points $t_m$ into the expression change patterns shown in FIG. 7 when asbestos is not applied as a stimulus.

The observation points in FIGS. 11A and 11B are time points of 0, 6, 12, 24, and 72 [hours], which are different from the observation points shown in FIG. 10 (FIG. 9). In this case, the number of genes in FIG. 11A is 16896 and the number of genes in FIG. 11B is 18159. Since the number of observation points $t_m$ in FIGS. 11A and 11B is 5, the number of types of the expression change patterns is $2^{(5-1)}$ as shown in FIG. 12.

From the test result shown in FIG. 10 and FIGS. 11A and 11B, it is confirmed that the second symmetric property that the numbers of genes in the patterns where the plus and the minus are inverted are symmetric is not changed, regardless of "type of cell", "presence of stimulus", and "interval between observation points".

The first symmetric property that the number of genes having a positive change and the number of genes having a negative change are symmetric is also confirmed in the test results shown in FIG. 10 and FIGS. 11A and 11B. This is matched with the above-mentioned proving. It is also confirmed that the first and second symmetric properties are not changed.

Therefore, the group of genes correlated with pairs of genes classified into the expression change patterns having the inverted relation by the classification section 24 can be said to be useful information which is a reliable indicator for multilateral analysis. For example, when the number of observation points $t_m$ increases, the genes to be detected can be narrowed. Accordingly, useful performance can be expected particularly for the detecting of genes changing in the opposite directions such as miRNA. For example, when the observation points $t_m$ are selected with a constant interval, it is possible to detect the time points when the expression level changes from a decrease (increase) to an increase (decrease) and it is thus possible to acquire the specific characteristics of the temporal variation of the genes.

3-1-2. Flow of Gene Classifying Process

Figure 13:
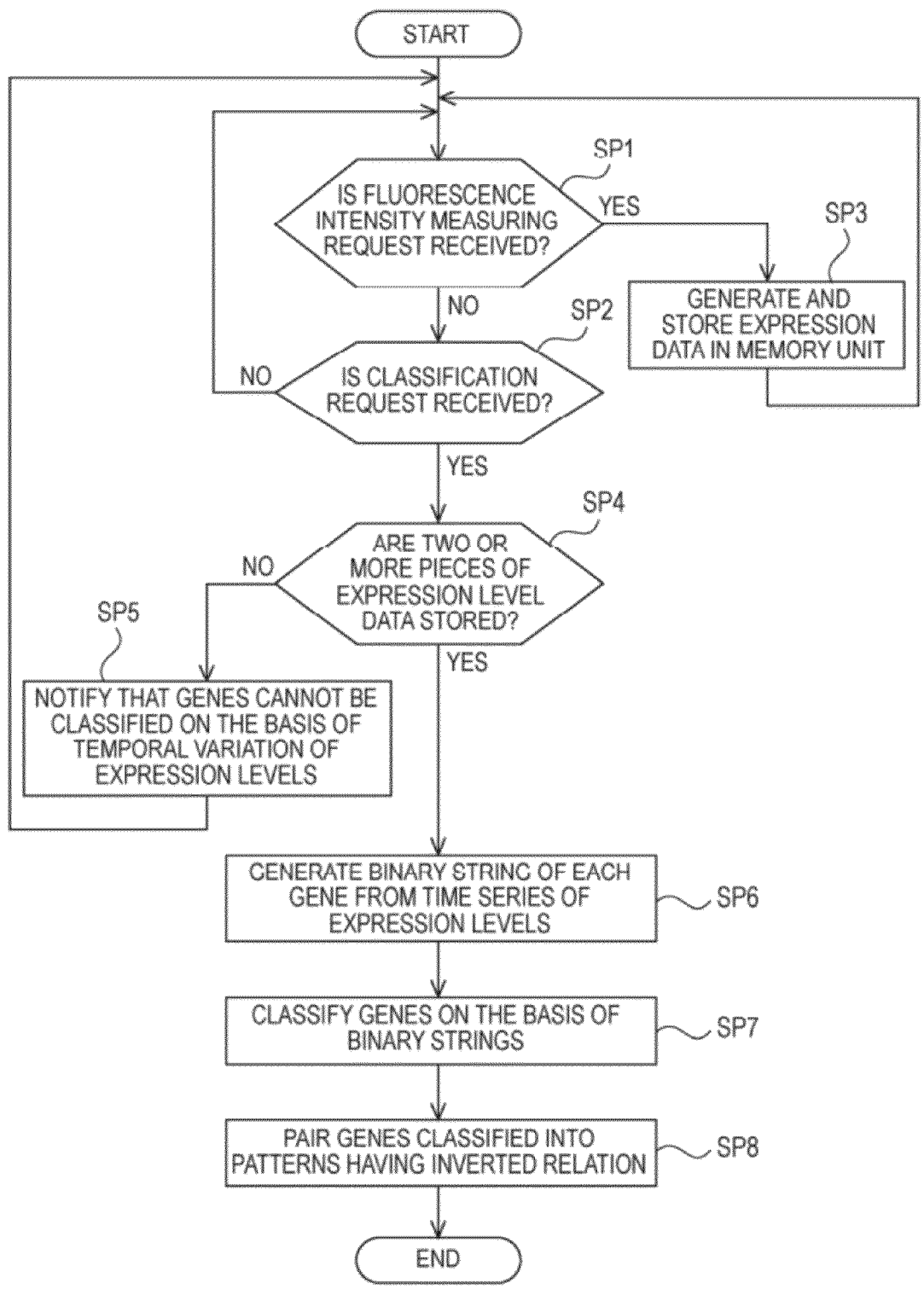
FIG. 13 is a flowchart illustrating a flow of a first gene classifying process.

The flow of the first gene classifying process will be described with reference to the flowchart shown in FIG. 13.

That is, the CPU 10 starts the flow of the gene classifying process, for example, using the power-on operation as a trigger, waits for a fluorescence intensity measuring request in the nucleic acid tip CP in step SP1, and waits for a gene classifying request in step SP2.

When receiving the fluorescence intensity measuring request, the CPU 10 serves as the fluorescence intensity acquiring section 21 (FIG. 4) in step SP3, allows the fluorescence intensity measuring device 3 (FIG. 1) to start its measurement, and waits for the measurement result from the fluorescence intensity measuring device 3. When receiving the fluorescence intensity data as the measurement result, the CPU 10 serves as the expression level calculating section 22 (FIG. 4). In this case, the CPU 10 generates the expression level data indicating the gene expression level from the fluorescence intensity data, stores the expression level data in the memory unit 14, and then performs the process of step SP1 again. When the fluorescence intensity data is not received within a predetermined time after the fluorescence intensity measuring device 3 (FIG. 1) starts the measurement, the CPU 10 performs the process of SP1 again without generating the expression level data.

On the other hand, when receiving the gene classifying request, the CPU 10 serves as the binarization section 23 (FIG. 4) in step SP4 and determines whether two or more pieces of expression level data exist in the memory unit 14 on the basis of the data stored in the memory unit 14.

Here, when it is determined that two or more pieces of expression level data do not exist in the memory unit 14, the CPU 10 notifies that the genes cannot be classified on the basis of the temporal variation of the gene expression levels in step SP5 and performs the process of step SP1 again.

On the contrary, when it is determined that two or more pieces of expression level data exist in the memory unit 14, the CPU 10 generates the expression level binary strings from the time series of the gene expression level $GE_n$ for each gene $G_n$ in step SP6 (FIG. 5).

The CPU 10 serves as the classification section 24 (FIG. 4) in step SP7 and recognizes $2^{(m-1)}$ expression change patterns based on the number of observation points $t_m$. Then, the CPU 10 classifies the genes $G_n$ into the $2^{(m-1)}$ expression change patterns (FIG. 6) on the basis of the expression level binary strings of the genes $G_n$.

In step SP8, the CPU 10 pairs the genes classified into the expression change patterns having the inverted relation out of the genes $G_n$ classified into the plural expression change patterns in step SP8 and ends the flow of the gene classifying process.

In this way, the CPU 10 performs the gene classifying process in accordance with the gene classifying program.

3-1-3. Advantage and Others

The flow of the first gene classifying process has been described above. That is, the gene classifying device 4 generates the binary strings (expression level binary strings) by taking the positive or negative differences in the gene expression level $GE_n$ in the temporal passage direction of the observation points $t_m$ for each gene $G_n$ (FIG. 5).

The gene classifying device 4 classifies the genes $G_n$ on the basis of all of the different plus and minus patterns (expression change patterns (FIG. 6)) that the expression level binary strings can have and the expression level binary strings generated for each gene $G_n$.

In this way, the gene classifying device 4 can necessarily acquire the patterns (expression change patterns) that the expression level binary strings can have by converting the expression levels $GE_n$ at the observation points $t_m$ into binary strings (expression level binary strings) paying attention to the "increasing" or "decreasing" variation in the temporal passage direction of the observation points $t_m$. Therefore, the gene classifying device 4 can simply pattern the variations of the genes $G_n$ on the basis of the temporal variation thereof.

In addition, it is possible to greatly reduce the time (load) required for the classification, compared with the case where the genes $G_n$ are classified into patterns on the basis of all combinations of two different genes out of several tens of thousands of genes without converting the expression levels $GE_n$ at the observation points $t_m$ into binary strings (expression level binary strings) paying attention to the "increasing" or "decreasing" variation in the temporal passage direction of the observation points $t_m$.

The gene classifying device 4 pairs the genes classified into the expression change patterns in which the binary strings are inverted. The number of genes is regardless of the "type of cell", the "presence of stimulus", and the "interval between observation points", as shown in FIG. 9 to FIG. 11B.

Therefore, the gene classifying device 4 can simply specify the genes acting in the opposite ways with predetermined precision, which can be utilized as a new indicator with high reliability for the multilateral analysis. This is particularly useful for analyzing details of the genes varying in the opposite directions, such as the detection of miRNA.

In the first gene classifying process, it is possible to simply classify the genes on the basis of the temporal variation of the gene expression levels, by classifying the genes $G_n$ on the basis of the binary strings (expression level binary strings) acquired by taking the plus or minus differences in gene expression level $GE_n$ in the temporal passage direction of the observation points $t_m$ for each gene $G_n$.

3-2. Second Gene Classifying Process

3-2-1. Functional Configuration

Figures 14, 15:
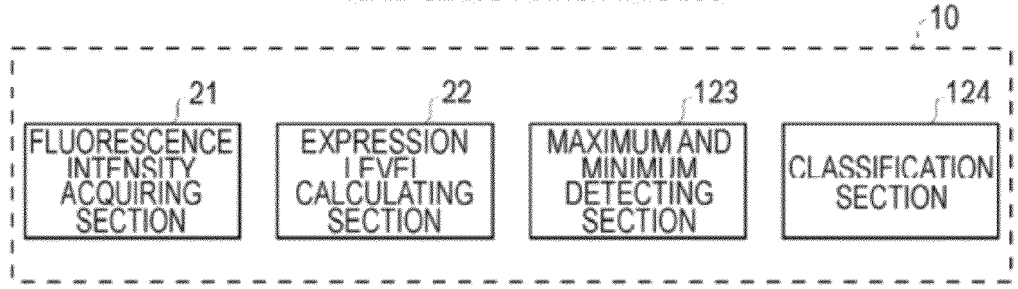
FIG. 14 is a block diagram illustrating the functional configuration (2) of the CPU for performing the gene classifying process.
FIG. 15 is a diagram schematically illustrating a combination pattern including pairs of two observation points when the number of observation points is 5.

In the second gene classifying process, the CPU 10 serves as a fluorescence intensity acquiring section 21, an expression level calculating section 22, a maximum and minimum detecting section 123, and a classification section 124 in accordance with the gene classifying program, as shown in FIG. 14 in which the same elements as shown in FIG. 5 are referenced by the same reference numerals.

As shown in FIG. 14, in the second gene classifying process, the binarization section 23 and the classification section 24 (FIG. 5) in the first gene classifying process are replaced with the maximum and minimum detecting section 123 and the classification section 124.

Specifically, the genes are classified on the basis of the temporal variation of the gene expression levels in the first gene classifying process, but the genes are classified on the basis of the times when the gene expression levels reach the maximum or the minimum in the second gene classifying process.

The maximum and minimum detecting section 123 waits for the gene classifying request and recognizes the gene expression levels $GE_n$ at the observation points $t_m$ on the basis of the tip identification data and the expression level data stored in the memory unit 14, when receiving the gene classifying request.

Here, when only the gene expression level $GE_1$ at a single observation point $t_1$ is recognized, it means that the times when the gene expression levels in the target cell reach the maximum or the minimum cannot be specified. In this case, the maximum and minimum detecting section 123 notifies the fact, for example, using the display unit 16.

On the contrary, when the gene expression levels $GE_n$ at two or more observation points $t_m$ are recognized, the maximum and minimum detecting section 123 detects the gene expression level GE having the maximum value and the gene expression level GE having the minimum value for each gene $G_n$.

In the example shown in FIG. 3, as for the gene $G_1$, the gene expression level GE at the observation point $t_m$ is detected as the maximum and the gene expression level GE at the observation point $t_2$ is detected as the minimum. As for the gene $G_2$, the gene expression level GE at the observation point $t_2$ is detected as the maximum and the gene expression level GE at the observation point $t_4$ is detected as the minimum.

The classification section 124 classifies the genes $G_n$ on the basis of combination patterns (hereinafter, referred to as "observation point combination pattern") in which two observation points $t_m$ are paired and the times (observation points) of the gene expression levels GE detected by the maximum and minimum detecting section 123.

The number of combination patterns of the maximum values and the minimum values (observation point combination pattern) at the observation points is the number of observation points $t_m \times$(the number of observation points–1), for example, $5 \times (5-1) = 20$ as shown in FIG. 15 when the number of observation points $t_m$ is 5.

In the example shown in FIG. 3 where the number of observation points $t_m$ is 5, the gene $G_1$ having the maximum at the observation point $t_5$ and the minimum at the observation point $t_2$ is classified into the observation combination pattern $(t_2, t_5)$ of "8" shown in FIG. 15. The gene $G_2$ having the maximum at the observation point $t_2$ and the minimum at the observation point $t_4$ is classified into the observation combination pattern $(t_2, t_4)$ of "7" shown in FIG. 15.

Specifically, as shown in FIG. 15, identifiers such as numbers are assigned to the observation point combination patterns and the identifier of the observation point combination of the maximum and minimum expression levels of each gene $G_n$ is added to the corresponding expression level data.

In addition, the classification section 124 pairs the genes of which the order of the maximum and the minimum is inverted out of the genes classified into the same observation point combination pattern.

For example, when the genes classified into "1" of the observation point combination patterns shown in FIG. 15 are $G_2$ and $G_{38}$, the gene $G_2$ has the maximum at the observation point $t_1$ and the minimum at the observation point $t_2$, and the gene $G_{38}$ has the minimum at the observation point $t_1$ and the maximum at the observation point $t_2$, data is generated which states that the genes $G_2$ and $G_{38}$ have the relation that the order of the maximum and the minimum is inverted.

Here, test results are shown in FIGS. 16A and 16B and FIGS. 17A and 17B. FIGS. 16A and 16B show the number of genes with an expression level having the maximum at the observation point s and the minimum at the observation point u and the number of genes with an expression level having the maximum at the observation point u and the minimum at the observation point s when asbestos is applied as a stimulus to A549 cell using E-GEOD-6013 as a sample (FIG. 16A) and when asbestos is not applied as a stimulus (FIG. 16B). In this case, the number of observation points, the time, and the number of genes in the test result shown in FIGS. 16A and 16B are the same as the test result shown in FIG. 7.

On the other hand, FIGS. 17A and 17B show the number of genes with an expression level having the maximum at the observation point s and the minimum at the observation point u and the number of genes with an expression level having the maximum at the observation point u and the minimum at the observation point s when asbestos is applied as a stimulus to Beas2A cell using E-GEOD-6013 as a sample (FIG. 17A) and when asbestos is not applied as a stimulus (FIG. 17B). In this case, the number of observation points, the time, and the number of genes in the test result shown in FIGS. 17A and 17B are the same as the test result shown in FIG. 10.

From the test results shown in FIGS. 16A and 16B and FIGS. 17A and 17B, it is confirmed that the number of genes with an expression level having the maximum at the observation point s and the minimum at the observation point u and the number of genes with an expression level having the maximum at the observation point u and the minimum at the observation point s have the symmetric property, regardless of the "type of cell", the "presence of stimulus", and the "interval between observation points".

The degree of correlation in distribution of the number of genes with an expression level having the maximum at the observation point s and the minimum at the observation point u and the number of genes with an expression level having the maximum at the observation point u and the minimum at the observation point s is "0.984" in FIG. 16A and "0.963" in FIG. 16B. The degree of correlation is "0.958" in FIG. 17A and "0.856" in FIG. 17B.

Therefore, the group of genes including the pairs of genes of which the order of the maximum and the minimum is inverted out of the genes classified in the same observation point combination pattern is useful information which is a reliable indicator for multilateral analysis and information from another point of view other than the first gene classifying process, similarly to the pairs in the first gene classifying process.

In the second gene classifying process, the special binarization process of the first gene classifying process is not performed and the genes can be classified only by detecting the maximum and minimum expression levels, thereby further simplifying the second gene classifying process than the first gene classifying process. However, the reduction of the process time is not a factor for determining the superiority and inferiority of the classification ability.

3-2-2. Flow of Gene Classifying Process

The gene classifying process flow of the second gene classifying process will be described now with reference to the flowchart shown in FIG. 18 where the same elements as shown in FIG. 12 are referenced by the same reference numerals.

That is, the CPU 10 receives a gene classifying request in step SP2 and performs the process of step SP106 when it is confirmed in step SP4 that two or more pieces of expression level data exist in the memory unit 14.

The CPU 10 serves as the maximum and minimum detecting section 123 (FIG. 14) in step SP106 and detects the maximum gene expression level GE and the minimum gene expression level GE of each gene $G_n$.

Then, the CPU 10 serves as the classification section 124 (FIG. 14) in step SP107 and classifies the genes $G_n$ on the basis of the observation point combination patterns (FIG. 15) that the pairs of two observation points $t_m$ can have and the times (observation points t) when the maximum and minimum gene expression levels GE are detected by the maximum and minimum detecting section 123.

The CPU 10 pairs the genes of which the order of the maximum and the minimum is inverted out of the genes classified into the same observation point combination pattern in step SP108 and ends the gene classifying process flow.

In this way, the CPU 10 performs the gene classifying process in accordance with the gene classifying program.

3-2-3. Advantage and Others

The second gene classifying process has been described hitherto. That is, the gene classifying device 4 detects the maximum gene expression level GE and the minimum gene expression level GE of each gene $G_n$.

Then, the gene classifying device 4 classifies the genes $G_n$ on the basis of the combination patterns (observation point combination patterns (FIG. 15)) that the pairs of two observation points $t_m$ can have and the times (observation points t) when the maximum and minimum gene expression levels GE are detected by the maximum and minimum detecting section 123.

Since the gene classifying device 4 classifies the genes into the combination patterns (observation point combination patterns (FIG. 15)) necessarily acquired depending on the number of observation points without conversion into the binary strings like the first gene classifying process, it is possible to greatly reduce the time (load) required for the classification, compared with the first gene classifying process. However, the reduction of the process time is not a factor for determining the superiority and inferiority of the classification ability.

In addition, the genes $G_n$ may be patterned using a criterion (the time point when the gene expression level reaches the maximum or the minimum) other than the classification criterion of the first gene classifying process.

The gene classifying device 4 pairs the genes of which the order of the maximum and the minimum is inverted out of the genes classified into the same observation point combination pattern. The number of genes is not changed, regardless of the "type of cell", the "presence of stimulus", and the "interval between observation points", as shown in FIGS. 16A and 16B and FIGS. 17A and 17B.

Therefore, the gene classifying device 4 can simply specify the pairs of genes of which the observation point having the maximum value and the observation point having the minimum value with predetermined precision from a point of view different from the first gene classifying process, and the pairs of genes can be utilized as a new indicator with high reliability for the multilateral analysis. This is useful particularly for analyzing details of the genes varying in the opposite directions, such as the detection of miRNA.

According to the second gene classifying process, by classifying the genes $G_n$ into the combination patterns of the observation points having the maximum value and the observation points having the minimum values, it is possible to simply classify the genes into patterns on the basis of the times when the gene expression levels reach the maximum or the minimum.

4. Other Embodiments

In the above-mentioned embodiments, the gene expression levels $GE_n$ of a plurality of genes $G_n$ at a plurality of observation points $t_m$ are acquired by calculating the gene expression levels from the fluorescence intensity measured by the fluorescence intensity measuring device 3. However, the invention is not limited to the embodiments.

For example, the gene expression levels can be directly acquired by extracting mRNAs expressed in a target cell and breeding the mRNA into a predetermined amount using a real-time PCR (Polymerase Chain Reaction).

For example, the expression level data can be acquired by reading data indicating the fluorescence intensity from a data storage medium and calculating the expression level data from the read data. For example, the data indicating the gene expression levels can be acquired from a data storage medium. These acquisition methods can be combined. When the data is acquired from the data storage medium, for example, data obtained from various experimental places located remotely can be compared with each other and thus the further multilateral analysis can be carried out.

Examples of the data storage medium include package medium such as flexible disks, CD-ROMs (Compact Disk-Read Only Memory), and DVDs (Digital Versatile Disk), or semiconductor memories or magnetic disks in which data is temporarily or permanently stored. Wired or wireless communication mediums such as local area networks, the Internet, or digital satellite broadcast can be used.

In the above-mentioned embodiment, the binary strings acquired by taking the positive or negative differences in gene expression level $GE_n$ in the temporal passage direction of the observation points $t_m$ are expressed as a plus or a minus. However, this method of expressing binary strings is not limited to plus or minus, but various different methods of expression such as "0" or "1" can be applied.

In the above-mentioned embodiment, the genes classified into the expression change patterns in which the binary strings are inverted or the genes in which the combinations of the observation point having the maximum value and the observation point having the minimum value are inverted are paired. In addition to this pairing or instead of this pairing, another correlation may be performed. As a specific example of the correlation, the stimulus applied to the target cell is correlated with the expression change pattern or the observation point combination pattern into which the most genes are classified. This is only an example, and various correlations may be made depending on the details of the analysis.

Items that can be correlated may be recorded in a database and a setting step of setting items to be correlated from the database may be provided. Instead of setting the items from the database, the items to be correlated may be received from the operation unit 13 and the items input from the operation unit 13 may be set.

In the above-mentioned embodiments, the target genes are correlated as pairs using the second symmetric property (the numbers of genes in the patterns of which the plus and minus are inverted are symmetric) or the property (hereinafter, referred to as "third symmetric property") that the numbers of genes in which the combinations of the observation point having the maximum value and the observation point having the minimum value are inverted are symmetric. It may be assayed whether the gene expression levels to be acquired are good or poor (that is, whether the acquired gene expression levels are good or poor) using the second symmetric property, or the third symmetric property, or the first symmetric property.

Specifically, when the first symmetric property is used, a step of detecting the number of genes having a positive change between the observation point $t_m$ and the observation point $t_{m+1}$ and the number of genes having a negative change, as shown in FIG. 7, on the basis of the binary strings generated in step SP6, determining the reliability of the gene expression level to be bad when the value indicating the correlation between the numbers is equal to or greater than a threshold value, and notifying that the gene expression level $GE_n$ at the observation point $t_{m+1}$ should be discarded or correcting the gene expression level is provided, for example, between steps SP6 and SP7. This correction can employ the normalization technique described in, for example, Japanese Patent Application No. 2008-212625 suggested by the inventor. The assaying step may be performed after the correction.

In the normalization technique described in Japanese Patent Application No. 2008-212625, the gene expression level $GE_n$ at the observation point $t_m$ is converted to a ratio of, for example, the expression level $GE_1$ at the observation point $t_1$ and the gene expression level $GE_n$ is corrected so that the peak of the frequency distribution of the ratios moves in parallel to a reference ratio.

On the other hand, when the second symmetric property is used, a step of detecting the numbers of genes classified into the plus and minus patterns in which the binary strings are inverted, determining the reliability of the gene expression level to be bad when the value indicating the correlation between the numbers is equal to or greater than a threshold value, and notifying that the gene expression levels $GE_n$ at the observation points $t_m$ should be re-acquired, or re-classifying the genes after correcting the gene expression levels is provided, for example, after step SP8.

On the other hand, when the third symmetric property is used, a step of detecting the numbers of genes in which the combinations of the observation point having the maximum value and the observation point having the minimum value are inverted, determining the reliability of the gene expression level to be bad when the value indicating the correlation between the numbers is equal to or greater than a threshold value, and notifying that the gene expression levels $GE_n$ at the observation points $t_m$ should be re-acquired, or re-classifying the genes after correcting the gene expression levels is provided, for example, after step SP4 or step SP108.

As described above, the second symmetric property and the third symmetric property are not influenced by the "type of cell", the "presence of stimulus", or the "interval between observation points." Since the first symmetric property is correlated with the second symmetric property as described above, the same as for the second symmetric property can be said. Therefore, the damage of the first symmetric property, the second symmetric property, or the third symmetric property means that the gene expression levels $GE_n$ are different from true values.

In other words, the damage of the first symmetric property, the second symmetric property, or the third symmetric property means that a difference exists in external stress on a sample cell to be extracted or the condition or skill for extracting mRNA from the sample cell and components due to the difference are included in the gene expression levels $GE_n$. That is, the first symmetric property, the second symmetric property, or the third symmetric property serves as an indicator having excellent reliability for assaying the goodness and badness of the classification of genes. This was confirmed by the inventor and is also disclosed, for example, in Japanese Patent Application No. 2008-212625.

In the above-mentioned embodiments, one of the first and second gene classifying processes is performed, but both processes may be performed. In this case, as shown in FIG. 19 in which the same elements as shown in FIGS. 13 and 18 are referenced by the same reference numerals, the CPU 10 performs the process of step SP200 after step SP4.

The CPU 10 serves as a process selecting section in step SP200 and allows a user to select one of the temporal variations of the gene expression level and the time when the gene expression level reaches the maximum or the minimum as the item to which attention should be paid in classifying the genes, for example, by the use of the GUI function of the display unit 16.

Here, when the temporal variation of the gene expression level is selected as the item to which attention should be paid in classifying the genes, the CPU 10 performs the processes of steps SP6 to SP8. On the other hand, when the time when the gene expression level reaches the maximum or the minimum is selected as the item to which attention should be paid in classifying the genes, the CPU 10 performs the processes of steps SP106 to SP108.

Accordingly, the CPU 10 can simply classify the genes with predetermined precision from two points of view and thus the result can be utilized as a reliable indicator for the multilateral analysis.

In the above-mentioned embodiment, the amount of complementary strands formed by the target nucleic acids and the nucleic probes is optically measured as the emission intensity. However, the measuring method is not limited to the embodiment. For example, a quantity of electricity or impedance may be used electromagnetically. An amount of complementary strands formed by target nucleic acids and nucleic acid probes and sensed by a sensor for sensing a predetermined physical quantity can be used. For example, a Stanford type made by Affymetrix, Inc. can be employed as the nucleic acid tip CP or others can be employed.

In the above-mentioned embodiment, the nucleic acid tip CP is used as the formation location of the complementary strands by the target nucleic acids and the nucleic acid probes. However, the formation location is not limited to the nucleic acid tip. For example, a tissue slice or a test tube can be employed as the formation location or other formation locations can be employed.

In the above-mentioned embodiment, the MAS is employed to calculate the gene expression level. However, the calculation method is not limited to this method, but any calculation method can be employed as long as it includes a normalization process of scaling the entire values about a reference value. The reason for including at least the normalization process of scaling the entire values about a reference value is based on the idea that the total amount of mRNA is biologically constant. The details thereof are described, for example, in Japanese Patent Application No. 2008-212625.

For example, the MAS of scaling the entire values with respect to the average or the normalization used in Japanese Patent Application No. 2008-212625 may be used as the normalization process of scaling the entire values with respect to a reference value.

The invention is usable in the field of biological industries such as gene testing, creation and preparation of medicines, or patient follow-up.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A gene classifying method comprising:
   acquiring expression levels of a plurality of genes at a plurality of observation points using a fluorescence intensity measuring device;
   generating a binary string by taking a positive or negative difference in expression level in a temporal passage direction of the observation points for each gene relative to a prior measurement; and
   classifying the genes using a gene classifying device on the basis of all plus and minus patterns that the binary strings can have and the generated binary strings.

2. The gene classifying method according to claim 1, further comprising:
   correlating the genes classified into the plus and minus patterns in which the binary strings have an inverted relation with each other as a pair from the genes classified in the plus and minus patterns.

3. The gene classifying method according to claim 1, further comprising:
   detecting a maximum expression level and a minimum expression level of each gene; and
   selecting one of a temporal variation of the expression level and a time when the expression level reaches the maximum or the minimum as an item to which attention should be paid in classifying the genes,
   wherein the step of detecting the maximum expression level and the minimum expression level is started when the time when the expression level reaches the maximum expression level or the minimum expression level is selected,
   wherein the step of generating the binary string is started when the temporal variation of the expression level is selected, and
   wherein the step of classifying the genes includes classifying the genes on the basis of combination patterns having pairs of two observation points and the observation points of the detected maximum and minimum expression levels and classifying the genes on the basis of all the plus and minus patterns that the binary strings can have and the generated binary strings.

4. A gene classifying computer program product stored on a non-transitory computer-readable medium including executable instructions that when executed by a processor performs steps for:
   acquiring expression levels of a plurality of genes at a plurality of observation points;
   generating a binary string by taking a plus or minus difference in expression level in a temporal passage direction of the observation points for each gene relative to an immediately prior measurement; and
   classifying the genes on the basis of all plus and minus patterns that the binary strings can have and the generated binary strings.

5. A gene classifying device comprising:
   acquiring means for acquiring expression levels of a plurality of genes at a plurality of observation points;
   generating means for generating a binary string by taking a plus or minus difference in expression level in a temporal passage direction of the observation points for each gene relative to an immediately prior measurement; and
   classifying means for classifying the genes on the basis of all plus and minus patterns that the binary strings can have and the binary strings generated by the generating means.

6. A gene classifying method comprising:
   acquiring expression levels of a plurality of genes at a plurality of observation points;
   detecting the maximum expression level and the minimum expression level of each gene; and
   classifying the genes on the basis of combination patterns including pairs of two observation points and the observation points of the detected maximum and minimum expression levels using a gene classifying device.

7. The gene classifying method according to claim 6, further comprising the step of pairing the genes of which the order of the maximum and minimum expression levels is inverted from the genes classified into the same combination pattern.

8. The gene classifying method according to claim 6, further comprising:
   generating a binary string by taking a plus or minus difference in expression level in a temporal passage direction of the observation points for each gene relative to an immediately prior measurement;
   selecting one of a temporal variation of the expression level and a time when the expression level reaches the maximum or the minimum as an item to which attention should be paid in classifying the genes,
   wherein the step of detecting the maximum expression level and the minimum expression level is started when the time when the expression level reaches the maximum expression level or the minimum expression level is selected, wherein the step of generating the binary string is started when the temporal variation of the expression level is selected, and wherein the step of classifying the genes includes classifying the genes on the basis of combination patterns having pairs of two observation points and the observation points of the detected maximum and minimum expression levels and classifying the genes on the basis of all the plus and minus patterns that the binary strings can have and the generated binary strings.

9. The gene classifying method according to claim 6, wherein the reliability of the acquired expression levels are classified depending on the basis of a degree of correlation in number between the genes of which the order of the maximum expression level and the minimum expression level is inverted out of the genes classified into the same combination pattern and, determining the reliability of the gene expression level to unreliable when the value indicating the correlation between the numbers is equal to or greater than a threshold value.

10. A gene classifying computer program product stored on a non-transitory computer-readable medium including executable instructions that when executed by a processor performs steps for:

acquiring expression levels of a plurality of genes at a plurality of observation points;

detecting a maximum expression level and a minimum expression level of each gene; and classifying the genes on the basis of combination patterns including pairs of two observation points and the observation points of the detected maximum and minimum expression levels.

11. A gene classifying device comprising:

acquiring means for acquiring expression levels of a plurality of genes at a plurality of observation points;

detecting means for detecting a maximum expression level and a minimum expression level of each gene; and classifying means for classifying the genes on the basis of combination patterns including pairs of two observation points and the observation points of the maximum and minimum expression levels detected by the detecting means.

12. A gene classifying device comprising:

an acquiring unit configured to acquire expression levels of a plurality of genes at a plurality of observation points;

a generating unit configured to generate a binary string by taking a plus or minus difference in expression level in a temporal passage direction of the observation points for each gene relative to a prior measurement; and a classifying unit configured to classify the genes on the basis of all plus and minus patterns that the binary strings can have and the binary strings generated by the generating unit.

13. A gene classifying device comprising:

an acquiring unit configured to acquire expression levels of a plurality of genes at a plurality of observation points;

a detecting unit configured to detect a maximum expression level and a minimum expression level of each gene; and a classifying unit configured to classify the genes on the basis of combination patterns including pairs of two observation points and the observation points of the maximum and minimum expression levels detected by the detecting unit.

* * * * *